(12) United States Patent
Maxwell et al.

(10) Patent No.: US 11,583,299 B1
(45) Date of Patent: *Feb. 21, 2023

(54) NONINVASIVE FRAGMENTATION OF URINARY TRACT STONES WITH FOCUSED ULTRASOUND

(71) Applicant: University of Washington through its Center for Commercialization, Seattle, WA (US)

(72) Inventors: Adam D. Maxwell, Woodinville, WA (US); Bryan W. Cunitz, Seattle, WA (US); Wayne Kreider, Seattle, WA (US); Oleg A. Sapozhnikov, Seattle, WA (US); Ryan S. Hsi, Seattle, WA (US); Michael R. Bailey, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 366 days.

This patent is subject to a terminal disclaimer.

(21) Appl. No.: 16/295,607

(22) Filed: Mar. 7, 2019

Related U.S. Application Data

(63) Continuation of application No. 14/268,414, filed on May 2, 2014, now Pat. No. 10,251,657.
(Continued)

(51) Int. Cl.
*A61B 17/22* (2006.01)
(52) U.S. Cl.
CPC ............ *A61B 17/22012* (2013.01); *A61B 2017/22014* (2013.01)

(58) Field of Classification Search
CPC ............ A61B 17/22004; A61B 17/225; A61B 2017/00146
See application file for complete search history.

(56) References Cited

U.S. PATENT DOCUMENTS

| | | | |
|---|---|---|---|
| 2005/0043726 A1* | 2/2005 | McHale | A61K 41/0028 606/27 |
| 2011/0054315 A1* | 3/2011 | Roberts | A61N 7/02 600/439 |

(Continued)

OTHER PUBLICATIONS

Eisenmenger, The Mechanisms of Stone Fragmentation in ESWL, Ultrasound in Med. & Biol., vol. 27, No. 5, 2001, pp. 683-693, USA.
(Continued)

*Primary Examiner* — Christopher L Cook
(74) *Attorney, Agent, or Firm* — Christensen O'Connor Johnson Kindness PLLC

(57) ABSTRACT

A method for attempting to fragment or comminute an object in a body using ultrasound includes producing a burst wave lithotripsy (BWL) waveform by a therapy transducer. The BWL waveform is configured to fragment or comminute the object. The BWL waveform includes a first burst of continuous ultrasound cycles and a second burst of continuous ultrasound cycles. A burst frequency corresponds to a frequency of repeating the bursts of the BWL waveform. The method also includes determining a cycle frequency f of the continuous ultrasound cycles within the first burst and the second burst based on a target fragment size D, where the cycle frequency is:

$f(\text{MHz}) = 0.47/D(\text{mm})$.

31 Claims, 22 Drawing Sheets

Related U.S. Application Data

(60) Provisional application No. 61/974,832, filed on Apr. 3, 2014, provisional application No. 61/818,822, filed on May 2, 2013.

(56) References Cited

U.S. PATENT DOCUMENTS

2011/0054363 A1* 3/2011 Cain ................... A61B 8/00
601/4
2012/0271167 A1* 10/2012 Holland ............ A61M 37/0092
600/439

OTHER PUBLICATIONS

Zhong, Stone Comminution Correlates With the Average Peak Pressure Incident on a Stone During Shock Wave Lithotripsy, Journal of Biomechanics, vol. 45, 2012, pp. 2520-2525, USA.

* cited by examiner

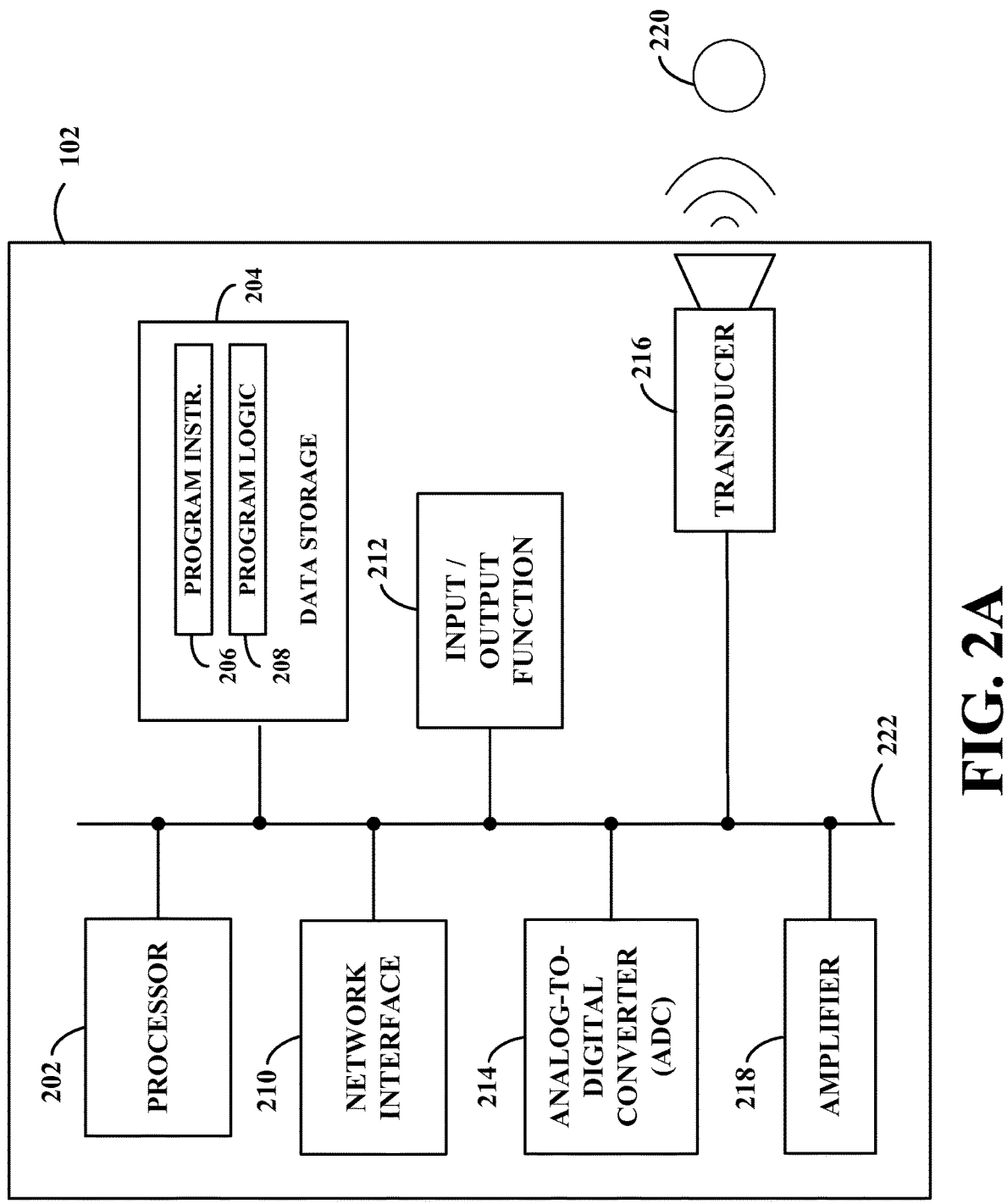

(Front View)

(Side View)

NONINVASIVE FRAGMENTATION OF URINARY TRACT STONES WITH FOCUSED ULTRASOUND

CROSS-REFERENCE TO RELATED APPLICATIONS

This application is a continuation of U.S. patent application Ser. No. 14/268,414, filed May 2, 2014, which claims the benefit to: (1) U.S. Provisional Patent Application No. 61/818,822, filed on May 2, 2013 and (2) U.S. Provisional Patent Application No. 61/974,832, filed on Apr. 3, 2014, both of which are herein incorporated by reference.

STATEMENT OF GOVERNMENT LICENSE RIGHTS

This invention was made with government support under grants 2R01EB007643-05, 2T32DK007779-11A1, 2P01DK043881-15, and 1R01DK092197-02, each awarded by the National Institutes of Health. The government has certain rights in the invention.

BACKGROUND

Unless otherwise indicated herein, the materials described in this section are not prior art to the claims in this application and are not admitted to be prior art by inclusion in this section.

Kidney stone disease generally involves minerals and salts in urine forming into crystals. In some instances, these crystals may cluster in the subject's body and accumulate into larger, rigid crystals or solid composites often referred to as kidney stones. In some instances, relatively smaller kidney stones may be able to pass out of the subject's body with urine, possibly unnoticed by the subject. However, relatively large kidney stones may block, stretch, and/or irritate the kidney and ureter, which connects the kidney to the bladder. Passing these larger kidney stones through the ureter may cause excruciating pain to the subject. In some instances, passing stones may contribute to urinary tract infections. Further, in some instances, obstruction by stones may contribute to the development of chronic kidney disease.

The prevalence of kidney stone disease is increasing. Studies have shown an increasing prevalence of this disease. Further, additional studies have indicated that approximately half of newly diagnosed subjects will have a recurrent stone within five to ten years of detecting a first kidney stone. In particular, recurrent stones may develop due to continuous stone crystallization over time or possibly growth of residual stone fragments after treatments.

Various treatments for kidney stone disease may require procedures underneath the skin of a subject. In some instances, these procedures may involve treating kidney stone disease in a subject without breaking the skin of the subject. During such treatments, it is important to perform such procedures in a calculated and efficient manner to prevent growth of residual stone fragments after such treatments.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Various non-invasive procedures face challenges with treating kidneys stones in a subject. As noted, kidney stones are generally formed of rigid crystals or solid composites. Further, as a general matter, these kidney stones are surrounded by soft and delicate tissues of the subject's internal organs. Thus, non-invasive procedures for treating kidney stones typically involve obstacles for fragmenting the kidney stones without harming the tissues surrounding the stones. An example of a non-invasive procedure is shockwave lithotripsy. During shockwave lithotripsy, cavitation may cause tissue injury in the kidney. As a result of the cavitation and the residual tissue injury, these procedures leave the subjects with damaged tissue in their kidneys, requiring a subsequent healing process. In some instances, the injury can also cause a permanent loss of functionality.

Various embodiments set forth herein provide ways of administering burst wave lithotripsy (BWL) to fragment kidney stones without affecting or harming surrounding tissues of the stones. In some embodiments, the BWL waveform is an acoustic waveform. These embodiments are provided herein for purposes of illustration and are not meant to be limiting in anyway.

In one aspect, a method for producing a burst wave lithotripsy (BWL) waveform using a computing device may be provided. The method may include determining a burst frequency for a number of bursts in the BWL waveform, where the number of bursts includes a first number of cycles. Further, the method may include determining a first cycle frequency for the first number of cycles. Yet further, the method may include determining a pressure amplitude for the BWL waveform, where the pressure amplitude is less than or equal to 8 MPa. In addition, the method may include determining a time period for producing the BWL waveform.

In another aspect, a computing device may include a processor and a physical and/or non-transitory computer-readable medium configured to store program instructions that, when executed by the processor, cause the computing device to carry out functions for producing a burst wave lithotripsy (BWL) waveform. The functions may include determining a burst frequency for a number of bursts in the BWL waveform, where the number of bursts includes a first number of cycles. Further, the functions may include determining a first cycle frequency for the first number of cycles. Yet further, the functions may include determining a pressure amplitude for the BWL waveform, where the pressure amplitude is less than or equal to 8 MPa. In addition, the functions may include determining a time period for producing the BWL waveform.

In yet a further aspect, a physical and/or non-transitory computer-readable medium may include program instructions that, when executed by a processor, cause the processor to perform functions for producing a burst wave lithotripsy (BWL) waveform. The functions may include determining a burst frequency for a number of bursts in the BWL waveform, where the number of bursts includes a first number of cycles. Further, the functions may include determining a first cycle frequency for the first number of cycles. Yet further, the functions may include determining a pressure amplitude for the BWL waveform, where the pressure amplitude is less than or equal to 8 MPa. In addition, the functions may include determining a time period for producing the BWL waveform.

The methods may comprise an in vivo method for fragmenting an object in a subject. The in vivo method may include administering an effective burst wave lithotripsy (BWL) waveform to a subject in need thereof to fragment an object in the subject. The method may result in complete or partial fragmentation of the object, and may lead to the subject being able to naturally pass the stone from the subject's body. The BWL waveform may be produced by any suitable method, including, but not limited to any embodiment or combination of embodiments of the production methods disclosed herein. The method for producing the BWL waveform may include determining a burst frequency for a number of bursts in the BWL waveform, where the number of bursts includes a first number of cycles. Further, method for producing the BWL waveform may include determining a first cycle frequency for the first number of cycles. Yet further, the method for producing the BWL waveform may include determining a pressure amplitude for the BWL waveform, where the pressure amplitude is less than or equal to 8 MPa. In addition, method for producing the BWL waveform may include determining a time period for producing the BWL waveform.

The subject in need thereof may be any suitable subject with an object in need of fragmenting, such as a mammal, including but not limited to a human. The subject may have any object in need of fragmenting, including but not limited to a urinary tract stone, a kidney stone, a ureter stone, a bladder stone, a urethra stone or a urethral stone, a prostate stone or a prostatic stone, a salivary stone, a gallbladder stone, a gall stone, a bile duct, a stone in the bile duct, a blood clot, blood, mucous, stool, cerumen, bodily tissue, a calcification, a calcified plaque, an atherosclerotic plaque, uric acid, struvite, calcium oxalate monohydrate (COM), cystine, a tonsil stone, an artificial object, and an object introduced inside the subject.

Administration of the effective BWL waveform may be carried out as deemed suitable by a physician or operator, possibly attending a subject. In some embodiments, a computing device may be used to control (and optionally calculate) the properties or parameters of a BWL waveform for treating a subject. In some embodiments, an operator of the computing device may set properties of the BWL waveform before treating a subject with an object (e.g., a kidney stone). In some instances, the operator may enter the properties of the BWL waveform in the computing device or a computer coupled to the computing device. As such, the computing device and/or the computer may create the BWL waveform and send the BWL waveform to an amplifier in the computing device. Further, the BWL waveform may be applied as a voltage to a transducer coupled to the computing device. Yet further, the transducer may be placed on the subject's skin and the BWL signal may be produced to fragment or comminute the kidney stone in the subject. It should be noted that one or more of the burst frequency for a number of bursts of a BWL waveform, the first cycle frequency for a first number of cycles, the pressure amplitude for the BWL waveform, and the time period for the BWL waveform may be predetermined as a setting of the computing device. In some embodiments, one or more predetermined settings of the computing device may be defined or standardized for producing the BWL waveform for fragmenting or comminuting the stone. In some embodiments, the setting may be adjusted based on the position, size, shape, composition, and/or properties of the stone.

In some embodiments, the computing device may determine the position, size, shape, composition, and/or properties of an object. Further, in some embodiments, the computing device may be coupled to a computer that displays an image of the object (e.g., a kidney stone). In some instances, an operator may view the images of the object and position the transducer to focus or align the BWL waveform with the stone. In some instances, the images of the kidney stone may be displayed in real-time as a video to determine whether the stone is fragmented and to what extent the stone is fragmented. Further, the imaging of the kidney stone may display the size of the fragments separated from the fragmented stone. In addition, the images may provide an indication of cavitation of the tissue surrounding or in the vicinity of the stone. As such, the imaging of the stone and the surrounding tissues may provide feedback signals to determine whether the BWL therapy should continue.

In an additional aspect, a system may include a means for producing a burst wave lithotripsy (BWL) waveform. Further, the system may include (a) a means for determining a burst frequency for a number of bursts in the BWL waveform, where the number of bursts includes a first number of cycles, (b) a means for determining a first cycle frequency for the first number of cycles, (c) a means for determining a pressure amplitude for the BWL waveform, where the pressure amplitude is less than or equal to 8 MPa, and (d) a means for determining a time period for producing the BWL waveform. These as well as other aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrative embodiments by way of example only and, as such, that numerous variations are possible. For instance, structural elements and process steps can be rearranged, combined, distributed, eliminated, or otherwise changed, while remaining within the scope of the embodiments as claimed.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2A shows a simplified block diagram of a network-access device to implement one or more example embodiments.

DETAILED DESCRIPTION

In the following detailed description, reference is made to the accompanying Figures, which form a part thereof. In the Figures, similar symbols typically identify similar components, unless context dictates otherwise. The illustrative embodiments described in the detailed description, Figures, and claims are not meant to be limiting. Other embodiments may be utilized, and other changes may be made, without departing from the spirit or scope of the subject matter presented herein. It will be readily understood that aspects of the present disclosure, as generally described herein, and illustrated in the Figures, can be arranged, substituted, combined, separated, and/or designed in a wide variety of different configurations, all of which are explicitly contemplated herein.

1. Overview

In some embodiments, various properties of a burst wave lithotripsy (BWL) waveform may be determined for producing the BWL waveform. As such, in some instances, the BWL waveform may be produced to fragment or comminute (e.g., reducing the object from a given size to a smaller size) an object.

For example, a burst frequency for a number of bursts of a BWL waveform may be determined. In some instances, one of the bursts may include a number of cycles. As such, a cycle frequency for the number of cycles may be determined. Further, a pressure amplitude for the BWL waveform may be determined. In some instances, the pressure amplitude may be less than or equal to 8 MPa. Yet further, a time period for producing the BWL waveform may be determined.

In some embodiments, a computing device may determine properties of the BWL waveform for producing the BWL waveform. In some instances, a transducer coupled to the computing device may produce the BWL waveform. For example, the transducer may be positioned outside of a subject (e.g., a human person, an animal, or any mammal) and an object may be positioned inside of the subject. As such, the computing device may cause the transducer to produce a BWL waveform that penetrates through the subject's tissues, traverses to the object in subject, and fragments or comminutes the object.

In some embodiments, the computing device may also produce imaging signals. In particular, a transducer coupled to the computing device may produce imaging signals that penetrate through the subject's tissues, traverse to the object in the subject, and reflect from the object. As such, the reflected imaging signals may return to the computing device and/or the transducer. Such reflected imaging signals may be referred to as a feedback signals. In some instances, based on these feedback signals, the computing device and/or an output device (e.g., a graphical display) coupled to the computing device may generate an image of an object and tissues surrounding the object. In particular, the computing device may utilize ultrasound to generate an image of the object.

2. Example Architecture

Figure 1:
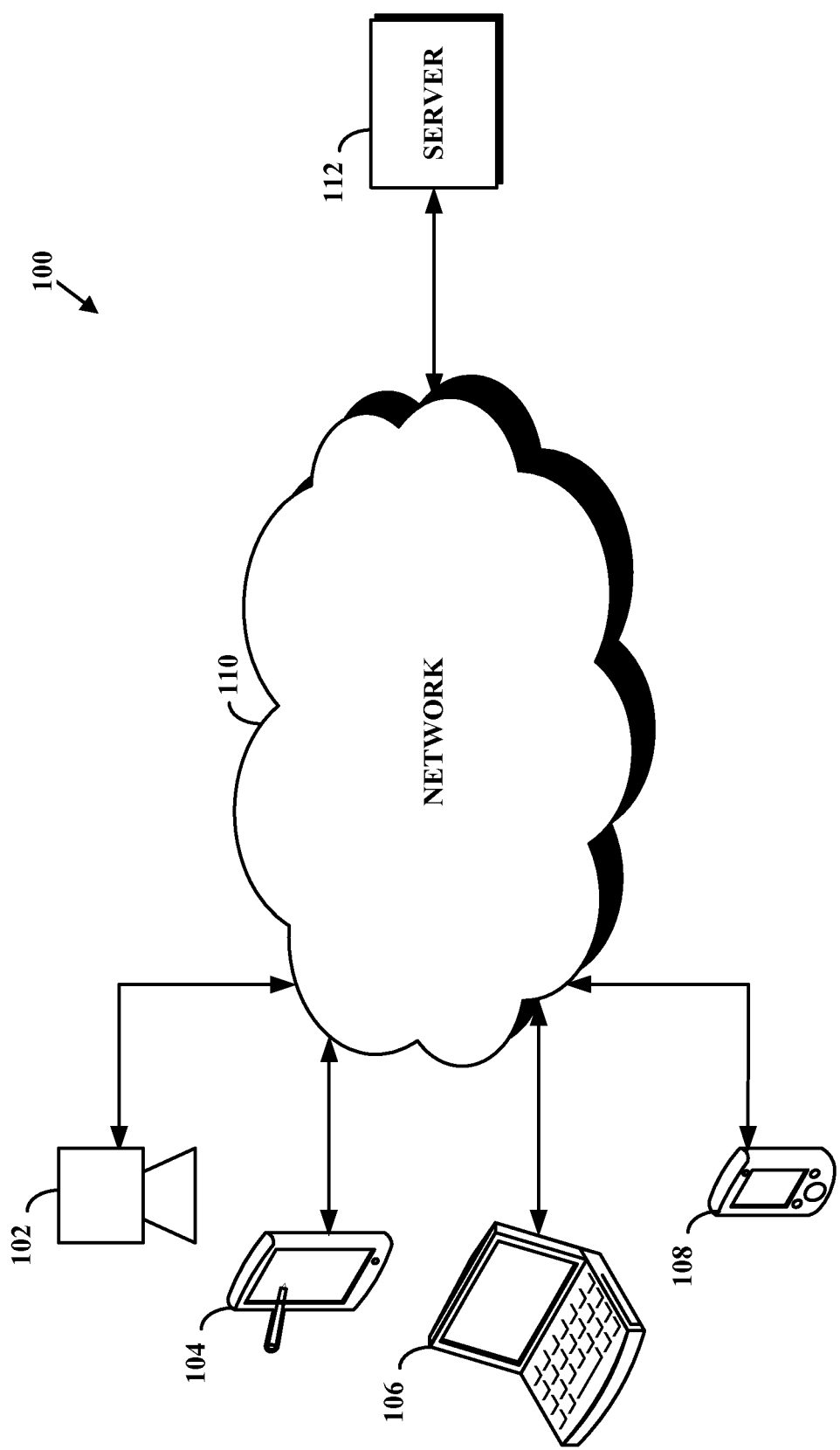
FIG. 1 shows a simplified block diagram of an example communication network to implement one or more example embodiments.

FIG. 1 shows a simplified block diagram of an example communication network to implement one or more example embodiments. It should be understood that this and other arrangements described herein are set forth only as examples. Those skilled in the art will appreciate that other arrangements, functions, orders, groupings of functions, and elements (e.g., medical devices, laboratory equipment, clinical tools, related interfaces, etc.) can be used instead and that some elements may be omitted altogether. Further, many of the elements described herein are functional entities that may be implemented as discrete or distributed components or in conjunction with other components and/or in other suitable combinations and locations. Various functions described herein as being performed by one or more entities may be carried out by hardware, firmware, and/or software. And various functions described herein may be carried out by a processor executing instructions stored in memory.

As shown in FIG. 1, example network 100 includes various network-access devices 102 through 108, network 110 (e.g., the Internet), and server 112. As illustrated, network-access devices 102, 104, 106, and 108 may be a computing device (e.g., a portable medical device coupled with a transducer), a tablet computer, a laptop computer or a desktop personal computer (PC), and a mobile phone, respectively. It should be noted that network-access device 102 may be described and referred to as computing device 102 for carrying out processes, methods, and/or functions further described herein. As such, network-access devices 102 through 108, network 110, and server 112 may be described for purposes of illustrating that various processes, steps, and/or functions may be distributed and performed by such devices, networks, and/or servers. For example, network-access devices 104 through 108 may be coupled to network-access device 102 or may be stand-alone devices for carrying out various processes, methods, and functions described herein. Thus, it should be noted that additional entities and devices not depicted in FIG. 1 could be present as well.

Network 110 may be a public network or a private network (e.g., a local area network in one or more hospitals, health centers, laboratories, clinics, and/or a doctor's office). Network 110 may also include one or more wide area networks, one or more local area networks, one or more public networks such as the Internet, one or more private networks, wired networks, wireless networks, and/or networks of any other variety. Other network elements may be in communication with network 110 as well. Also, there could be one or more devices and/or networks making up at least part of one or more of the communication links depicted in FIG. 1. As an example, there could be one or more routers, switches, or other devices or networks on the communication links between network-access devices 102 through 108, network 110, and/or server 112. Each of network-access devices 102 through 108 may be any network-access device arranged to carry out the network-access device functions described herein. For example, devices in communication with network 110 (including, but not limited to, network-access devices 102 through 108 and server 112) may exchange data using a packet-switched protocol such as IP, and may be identified by an address such as an IP address.

Systems and devices in which example embodiments can be implemented will now be described in greater detail. In general, an example system may be implemented in and/or can take the form of a computing device. As noted, network-access device 102 may be referred to as computing device 102, possibly interchangeably. In an example embodiment, computing device 102 may include an engine capable of producing BWL waveforms. Further, computing device 102 may be capable of producing imaging signals and/or receiving feedback signals. Further, the computing device may be portable, hand-held, transferrable, and/or such that a single person may handle the computing device with a subject.

Server 112 may be any network server or other computing system arranged to carry out the server functions described herein including, but not limited to, those functions described herein. In particular, a feedback signal received by a sensor, a transducer, and/or a sensor associated with a transducer may be communicated to server 112 to identify whether an object is fragmented. The feedback signals may be correspond to various signals. For example, feedback signals may correspond to B-mode signals (e.g., speckle tracking signals), Doppler signals possibly for identifying twinkling artifacts, and passive or active cavitation detection. As such, network-access device 102 and server 112 may share processes, methods, and/or functions described herein for fragmenting or comminuting an object.

FIG. 2A shows a simplified block diagram of a network-access device to implement one or more example embodiments. For example, network-access device 102 may include processor 202, data storage 204, and network interface 210, all linked together via system bus, network, or other connection mechanism 222.

In some embodiments, administration of the effective BWL waveform may be carried out as deemed suitable by an operator of computing device 102. In some embodiments, computing device 102 may be used to control (and optionally calculate) the properties or parameters of a BWL waveform for treating a subject. In some embodiments, an operator of the computing device may set properties of the BWL waveform before treating a subject with object 220 (e.g., a kidney stone). In some instances, the operator may enter the properties of the BWL waveform in computing device 102 or a computer coupled to computing device 102. As such, computing device 102 and/or the computer may create the BWL waveform and send the BWL waveform to amplifier 218. Further, the BWL waveform may be applied as a voltage to transducer 216, possibly coupled to computing device 102. Yet further, transducer 102 may be placed on the subject's skin and the BWL signal may be produced to fragment or comminute object 220 in the subject.

It should be noted that one or more of the burst frequency, the first cycle frequency, the pressure amplitude, and the time period may be predetermined as a standard setting of computing device 102. In some embodiments, such predetermined or standardized settings of computing device 102 may be defined for producing the BWL waveform for fragmenting or comminuting object 220. In some embodiments, the setting may be adjusted based on the position, size, shape, composition, and/or properties of object 220.

In some embodiments, computing device 102 may determine the position, size, shape, composition, and/or properties of object 220. Further, in some embodiments, computing device 220 may be coupled to a computer that displays an image of object 220. In some instances, an operator may view the images of object 220 and position transducer 216 to focus or align the BWL waveform with object 220. In some instances, the images of object 220 may be displayed in real-time as a video to determine whether object 220 is fragmented and to what extent the object 220 is fragmented. Further, the imaging of object 220 may display the size of the fragments separated from the fragmented stone. In addition, the images may provide an indication of cavitation of the tissue surrounding or in the vicinity of object 220. As such, the imaging of object 220 and the surrounding tissues may provide feedback signals to determine the effectiveness of the treatment and whether the BWL therapy should continue.

Processor 202 may include one or more general purpose microprocessors, central processing units (CPUs), and/or dedicated signal processors. In addition, processor 202 may include one or more application specific integrated circuits (ASICs), digital signal processors (DSPs), and may be integrated in whole or in part with network interface 210. Data storage 204 may include memory and/or other storage components, such as optical, magnetic, organic or other memory disc storage, which can be volatile and/or non-volatile, internal and/or external, and integrated in whole or in part with processor 202. Data storage 204 may be arranged to contain (i) program instructions 206 and (ii) program logic 208 that are executable by processor 202. Data storage 204 may also store data that may be manipulated by processor 202 to carry out the various methods, processes, or functions described herein.

In some embodiments, these methods, processes, and functions can be implemented using hardware, firmware, software, and any combination of hardware, firmware, and/or software. Therefore, data storage 204 may include a physical, tangible, and/or non-transitory computer-readable medium, having stored thereon program instructions that, upon execution by one or more processors, cause computing device 102 to carry out any of the methods, processes, or functions disclosed in this specification or the accompanying drawings.

Although these components are described herein as separate data storage elements, the elements could just as well be physically integrated together or distributed in various other ways. For example, program instructions 206 may be maintained in data storage 204 separate from program logic 208, for easy updating and reference by program logic 208. Network interface 210 may enable network-access device 102 to send communication and receive communication.

Network interface 210 typically functions to communicatively couple network-access device 102 to networks, such as network 110. As such, network interface 210 may include a wired (e.g., Ethernet) and/or wireless (e.g., Wi-Fi, BLUETOOTH®, or a wide-area wireless connection) packet-data interface, for communicating with other devices, entities, and/or networks.

Input/output function 212 may facilitate user interaction with an example computing device 102. Input/output function 212 may comprise multiple types of human-interface devices that may include a user-input device, a keyboard, a mouse, a touch screen, a probe, a transducer, a sensor, and/or any other device that is capable of receiving input by a person. Similarly, input/output function 212 may comprise multiple types of output devices, such as a graphical display, a printer, one or more light emitting diodes (LEDs), a speaker configured to generate audible sounds, or any other device that is capable of providing output discernible to a user. Additionally or alternatively, example computing device 102 may support remote access from another device, via network interface 210 or via other interfaces (not shown), such an RS-232 or Universal Serial Bus (USB) port.

Computing device 102 may also receive signals through a sensor or another device, possibly connected through input/output function 212. For example, transducer 216 may receive feedback signals. For example, transducer 216 may produce imaging signals and receive feedback signals reflected from object 220 back to transducer 216. Reflected signals or feedback signals, possibly received by transducer 216, may be converted to digital signals through an analog-to-digital converter (ADC) 214. ADC 214 may be a 12-24 bit ADC converter configured to sample signals at a 10-30 MHz frequency. For example, imaging signals transmitted by transducer 216 may be received and converted to digital signals through ADC 214. In some instances, digitized signals from ADC 214 may also be processed in real-time using mathematical software platforms. In some instances, unmodified signal outputs from ADC 214 may identify characteristics of object 220. For example, signal outputs may identify characteristics of object 220 and/or characteristics of fragmenting object 220. It should be noted that computing device 102 may also include one or more digital-to-analog converters (not illustrated) that may be configured to transmit signals to transducer 216.

In some instances, computing device 102 may modify the feedback signals. In some instances, feedback signals may be modified by band-pass filters, analog filters, amplifiers, and clipping diodes (not shown in FIG. 2A). In particular, signals may be modified by an anti-aliasing band-pass filter with a 0.7 to 17 MHz bandwidth. Further, feedback signals may be amplified using time-gain compensation. Yet further, signals may be limited by a clipping diode. In some instances, the modification described herein may be implemented through signal processing software. It should be noted that the above-referenced modifications to the feedback signals may occur before being sampled by ADC 214.

Transducer 216 may produce pressure waveforms. Further, transducer 216 may produce BWL waveforms to fragment or comminute an object. BWL waveforms may include a burst, a cycle, a sequence of substantially similar cycles in a burst, a chirp burst, a sound wave, a pressure wave, an oscillating pressure wave, an ultrasound wave, an acoustic wave, an acoustic pressure wave, an arbitrary wave (e.g. a time reversal wave), and/or broadly focused ultrasound wave. In some embodiments, properties of a BWL waveform may be determined and these properties of the BWL waveform may be sent to transducer 216. As such, transducer 216 may produce the BWL waveform, possibly to fragment or comminute object 220. For example, transducer 216 may produce a BWL waveform in response to executing program instructions 206 stored in data storage 204. In some instances, transducer 216 may produce a BWL waveform in response to receiving the BWL waveform from input/output function 212 through other connection mechanism 222.

Transducer 216 may be curved or linear for producing BWL waveforms. In some instances, transducer 216 may operate to prevent surface heating. As described further below, intermittent production of BWL waveforms may be used to prevent such surface heating, among other possibilities. Transducer 216 may include an 8.4 cm aperture to produce, for example, a BWL waveform with a −6 dB beam width of 31 mm by 8 mm.

In some embodiments, transducer 216 may also be used for producing pushing ultrasound. In some instances, transducer 216 may push or move stones separately or in combination with fragmenting or comminuting stones. As such, transducer 216 may include 128 elements and may function with approximately from a 100 kHz to a 4 MHz operating frequency, among other possibilities. In some instances, transducer 216 may be configured to operate as a phased-array transducer with approximately 96 elements for functioning under approximately the 100 kHz to a 4 MHz operating frequency. The excitation of one or more elements of transducer 216 may generate a BWL waveform.

In some embodiments, BWL waveforms, possibly produced by transducer 216 in situ, may also include intensity such as a spatial peak pulse average intensity of approximately 100 to 2,100 W/cm$^2$. Further, BWL waveforms may include energy (e.g., a total energy) of approximately 0.1 mJ to 2 J. Yet further BWL waveforms may be measured by power (e.g., energy per time for both electric and acoustic power). Electric power may excite transducer 216 or an element of transducer 216. In some instances, the total energy may be delivered in approximately 20 to 40 bursts, amongst other larger ranges of bursts that may be delivered.

Amplifier 218 may receive and amplify waveforms. For example, a BWL waveform may be sent to amplifier 218 and the amplified BWL waveform may be produced by transducer 216 to fragment or comminute object 220. In one scenario, properties of a BWL waveform may be determined using a mathematical software platform (e.g., MATLAB code). As such, the mathematical software platform may create the BWL waveform. Further, the BWL waveform may be sent to an FPGA board (not shown in FIG. 2A) for synthesizing the BWL waveform. In some instances, the FPGA board may receive commands from a computer to synthesize the BWL waveform, possibly indicating computations for synthesizing the BWL waveform. Further, the FPGA board may enhance timing characteristics of the BWL waveform and the FPGA board may send the BWL waveform to other components. For example, the BWL waveform may be sent to amplifier 218. The amplifier 218 may have two inputs for a high voltage supply and a low voltage supply. Thus, amplifier 218 may output amplified BWL waveforms with a 400 volt peak-to-peak waveform. These amplified BWL waveforms may be sent to a matching network (not shown in FIG. 2A). Further, these BWL waveforms may be sent to transducer 216 for producing BWL waveforms. As such, the BWL waveforms may be produced with up to 30 kW of instantaneous peak power for approximately a 1 ms to a 10 ms burst duration.

Transducer 216 may be used to fragment or comminute an object 222 that may be in a subject. In particular, transducer 216 may be placed on the skin of the subject, possibly in close proximity to object 222. Object 222 may be one or more of a urinary tract stone, a kidney stone, a ureter stone or ureteral stone, a bladder stone, a urethra stone or a urethral stone, a prostate stone or a prostatic stone, a salivary stone, a gallbladder stone, a gall stone, a bile duct or a stone in the bile duct, a blood clot, blood, mucous, stool, cerumen, bodily tissue, a calcification, a calcified plaque, an atherosclerotic plaque, uric acid, struvite, calcium oxalate monohydrate (COM), cystine, a tonsil stone, an artificial object, and an object introduced inside the subject. Further, transducer 216 may be removable so as to operate while being physically separate from computing device 102. In particular, transducer 216 may independently produce BWL waveforms to fragment or comminute object 220 without any other devices and/or systems. In some examples, a separate system may determine properties of BWL waveforms that are produced through transducer 216. In some instances, transducer 216 may communicate remotely or physically separate from computing device 102, possibly with wireless signals through input/output function 212. In some instances, there may be several transducers similar to transducer 216 that may be move, remotely controlled by computing device 102. Further, transducer 216 may communicate directly through network 110 with sever 106, as illustrated in FIG. 1.

Figure 2B:
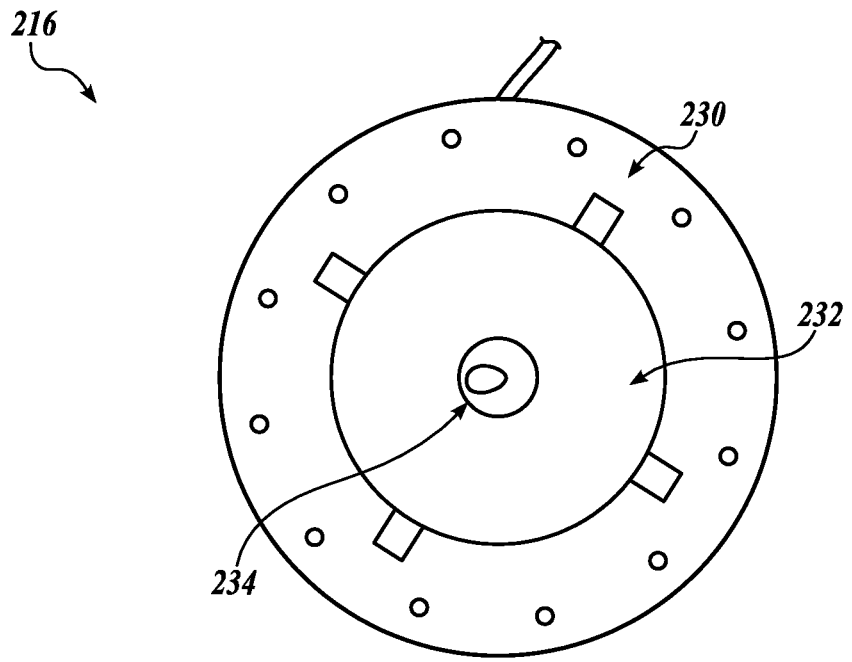
FIG. 2B shows a front view and a side view of a transducer to implement one or more example embodiments.

FIG. 2B shows a front view and a side view of a transducer. The transducer in FIG. 2B may, for example, be transducer 216 in FIG. 2A and is herein referred to as transducer 216. Transducer 216 may be operable, for example, in any of the manners described above in relation to FIGS. 1 and 2A. For example, as shown in FIG. 2B, transducer 216 may be operable while being physically separate from computing device 102. In FIG. 2B, a front view and a side view of transducer 216 are shown.

As shown in the front view, transducer 216 may include an exterior portion 230 for supporting the middle portion 232 of transducer 216. Further, the outer curvature of the housing around exterior portion 230 may have a diameter of approximately 130 mm. Yet further, the diameter of exterior portion 230 may be approximately 108 mm. In some instances, the middle portion 232 may include porous piezoelectric material filled with mineral oil. The diameter of the middle portion 232 may be approximately 84 mm and the radius of the curvature may be approximately 54 mm. The opening 234 may have a diameter of 17 mm. As shown in the side view, transducer 216 may be connected to computing device 102 through a wire on the backside of transducer 216. In one example, transducer 216 may produce BWL waveforms with a frequency of approximately 215 kHz.

Figure 3:
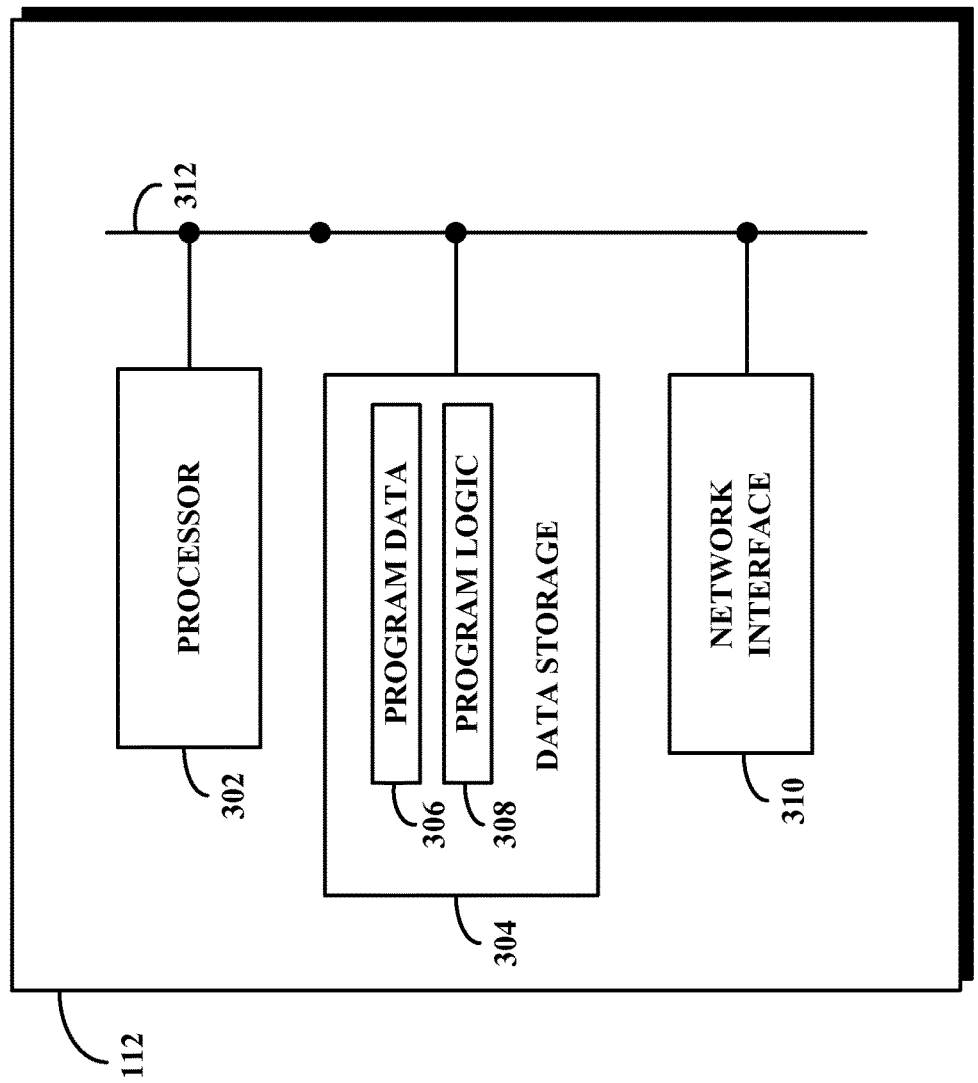
FIG. 3 shows a simplified block diagram of a server to implement one or more example embodiments.

FIG. 3 shows a simplified block diagram of a server to implement one or more example embodiments. As shown in FIG. 3, server 112 may include processor 302, data storage 304 including program data 306 and program logic 308, and network interface 310, all linked together via system bus, network, and/or other connection mechanism 312. Processor 302, data storage 304, program data 306, program logic 308, and network interface 310 may be configured and/or arranged similar to processor 202, data storage 204, program instructions 206, program logic 208, and network interface 210, respectively, as described above with respect to network-access device 102.

Data storage 304 may contain information used by server 112 in operation. For example, date storage 304 may include instructions executable by the processor for carrying out the server functions described herein including, but not limited to, those functions described below with respect to additional figures described below. As another example, data storage 304 may contain various design logic and/or design data used for determining a test result, such as the logic and data described below with respect to additional figures described below. Generally, data storage 304 may contain information used by server 112 to provide information accessible by various network-access devices, such as network-access device 102, over network 110.

Figure 4:
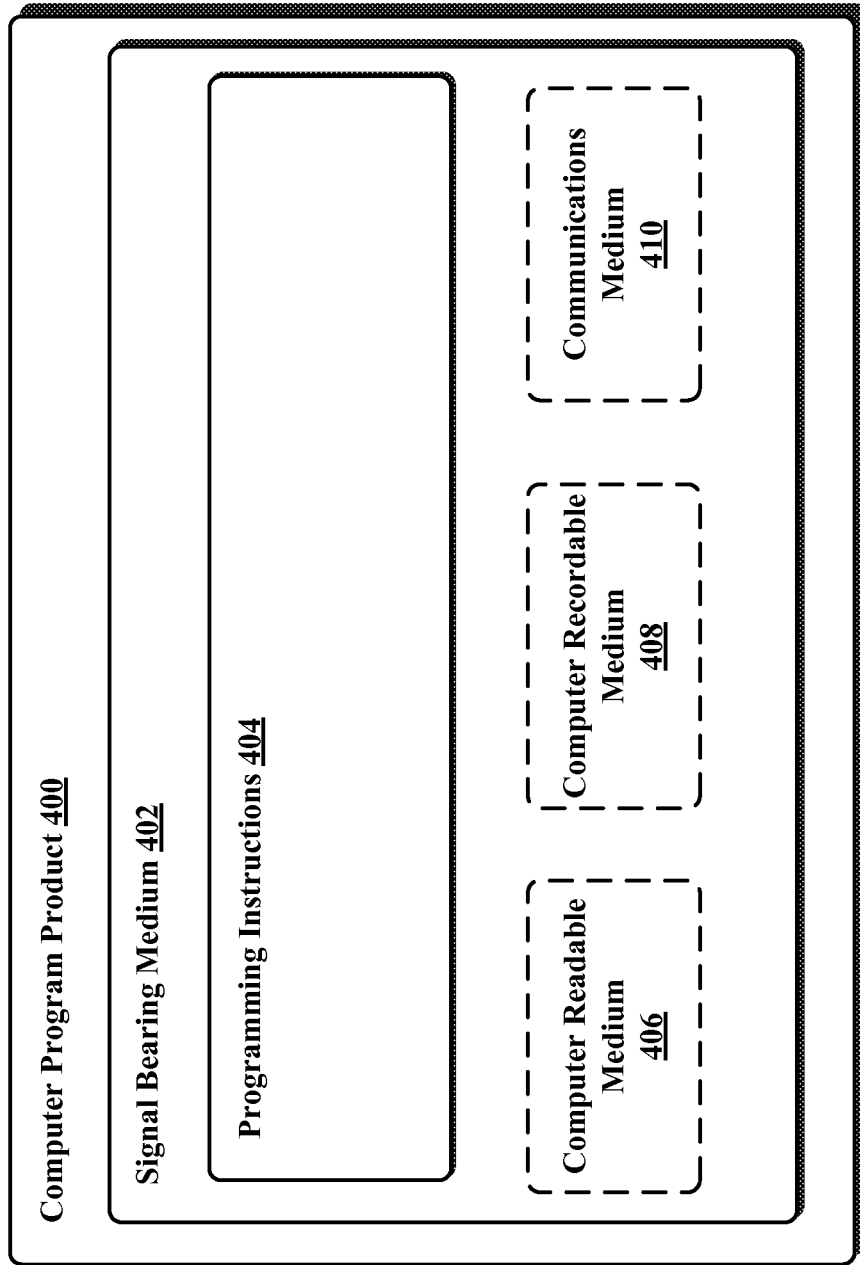
FIG. 4 shows an example computer-readable medium to implement one or more example embodiments.

As noted above, in some embodiments, the disclosed methods may be implemented by computer program instructions encoded on a physical and/or non-transitory computer-readable storage media in a machine-readable format, or on other physical and/or non-transitory media or articles of manufacture. FIG. 4 shows an example computer-readable medium to implement one or more example embodiments. Further, FIG. 4 may be a schematic illustrating a conceptual partial view of an example computer program product that includes a computer program for executing a computer process on a network-access device.

In one embodiment, the example computer program product 400 is provided using a signal bearing medium 402. The signal bearing medium 402 may include one or more programming instructions 404 that, when executed by one or more processors may provide functionality or portions of the functionality described herein. In some examples, the signal bearing medium 402 may encompass a computer-readable medium 406, such as, but not limited to, a hard disk drive, a Compact Disc (CD), a Digital Video Disk (DVD), a digital tape, memory, etc. In some implementations, the signal bearing medium 402 may encompass a computer recordable medium 408, such as, but not limited to, memory, read/write (R/W) CDs, R/W DVDs, etc.

In some implementations, the signal bearing medium 402 may encompass a communications medium 410, such as, but not limited to, a digital and/or an analog communication medium (e.g., a fiber optic cable, a waveguide, a wired communications link, a wireless communication link, etc.). Thus, for example, the signal bearing medium 402 may be conveyed by a wireless form of the communications medium 410. It should be understood, however, that computer-readable medium 406, computer recordable medium 408, and communications medium 410 as contemplated herein are distinct mediums and that, in any event, computer-readable medium 408 may be a physical and/or a non-transitory computer-readable medium.

Figure 2B:
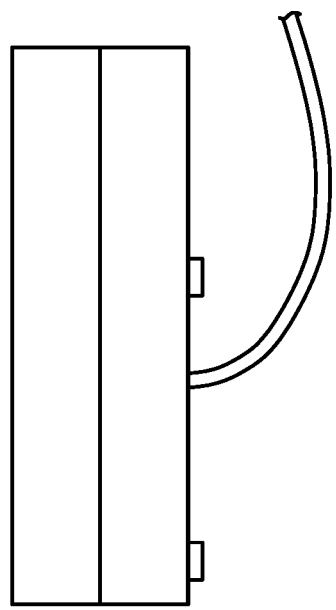

The one or more programming instructions 404 may be, for example, computer executable and/or logic implemented instructions. In some examples, a computing device such as the computing device 102 of FIGS. 1 through 2B may be configured to provide various operations, functions, or actions in response to the programming instructions 404 conveyed to the computing device 102 by one or more of the computer readable medium 406, the computer recordable medium 408, and/or the communications medium 410.

The physical and/or non-transitory computer readable medium could also be distributed among multiple data storage elements, which could be remotely located from each other. The computing device that executes some or all of the stored instructions could be a computing device or a network-access device such as computing device 102 illustrated in FIGS. 1 and 2A. Alternatively, the computing device that executes some or all of the stored instructions could be another computing device, such as a server, for instance server 112 illustrated in FIG. 3.

3. Example Methods of Producing a Burst Wave Lithotripsy (BWL) Waveform

In some embodiments, BWL waveforms may fragment or comminute an object using acoustic radiation force. Further, BWL waveforms may apply forces to the object in vivo to fragment or comminute the object without causing affecting or damaging the surrounding tissue or tissue layers. Yet further, BWL waveforms may be applied while receiving reflection signals for detecting whether the object is fragmented or comminuted.

Figure 5A:
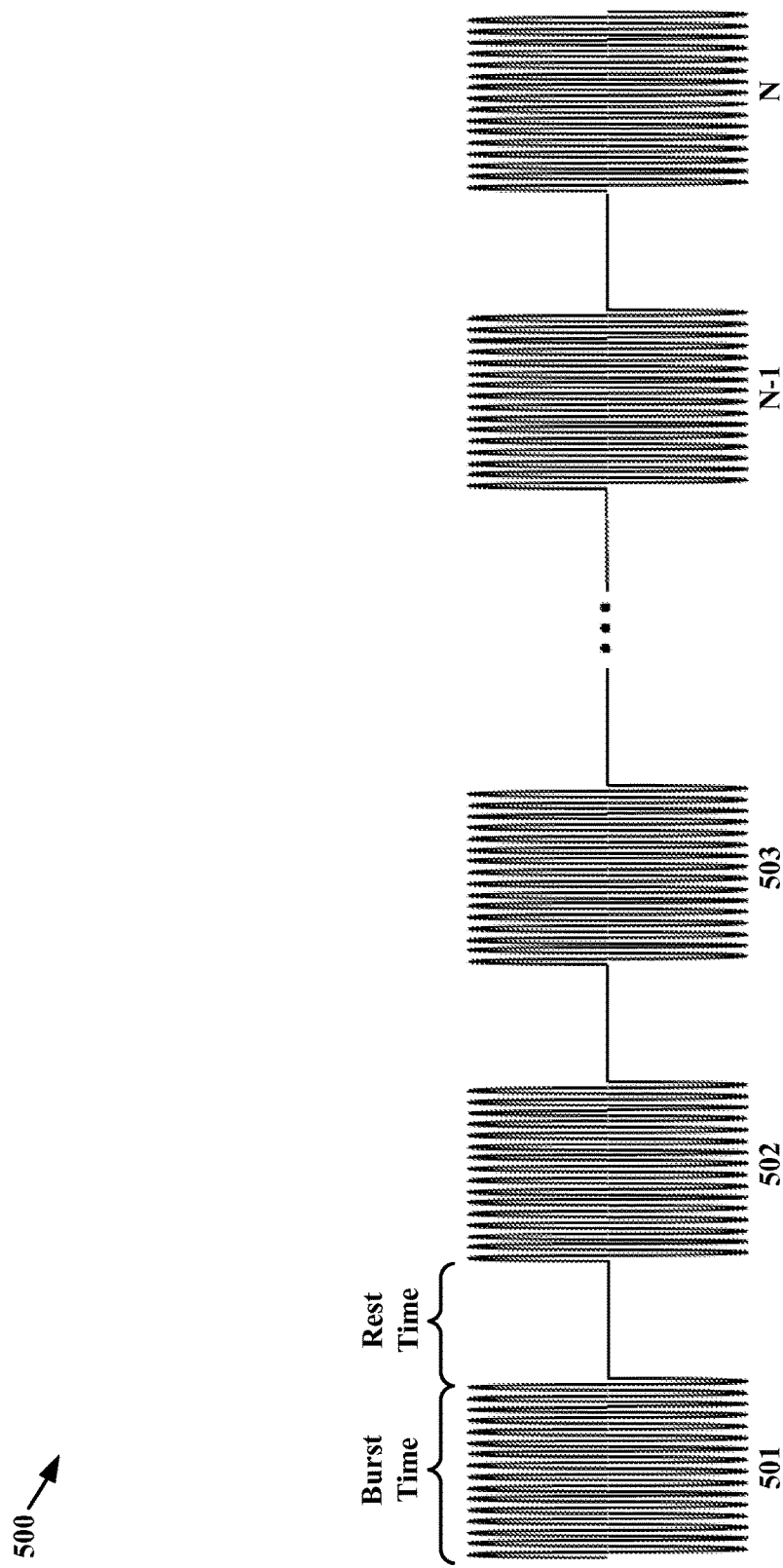
FIG. 5A shows aspects of a BWL waveform in accordance with one or more example embodiments.

FIG. 5A shows aspects of a BWL waveform in accordance with one or more example embodiments. In some embodiments, BWL waveform 500 may be produced, for example, in any of the manners described above in relation to FIGS. 1 through 4. For example, properties of BWL waveform 500 may be determined using a mathematical software platform (e.g., MATLAB code), creating BWL waveform 500 in graphical space. As such, BWL waveform 500 may be sent to a transducer, such as transducer 216 in FIGS. 2A through 2B. In some instances, transducer 216 may produce BWL waveform 500 to fragment or comminute object 220.

As shown in FIG. 5A, the BWL waveform 500 has a number of bursts, represented by the letter "N". In particular, BWL waveform 500 includes bursts 501, 502, and 503. In addition, BWL waveform 500 includes burst N-1 and burst N. As such, the number of bursts, represented by a number "N", may be any number of bursts. For example, the number of bursts, N, may represent the number of bursts to fragment or comminute an object. Thus, the number of bursts, N, may be determined for producing BWL waveform 500. In addition, as shown in FIG. 5A, a burst time period is illustrated for the duration of burst 500 and a rest time period is illustrated between burst 501 and burst 502. In addition, bursts 502, 503, N-1, and N may have burst time periods and rest time periods in between them. As such, combining the burst times and the rest times may amount to a time period for producing BWL waveform 500. The burst time period and the rest time period may range from approximately 1 microsecond to 333 milliseconds. In some embodiments, the rest time period may be any time period in between bursts 502, 503, N-1, and N. Further, the rest time period may vary with the burst frequency, for example.

Figure 5B:
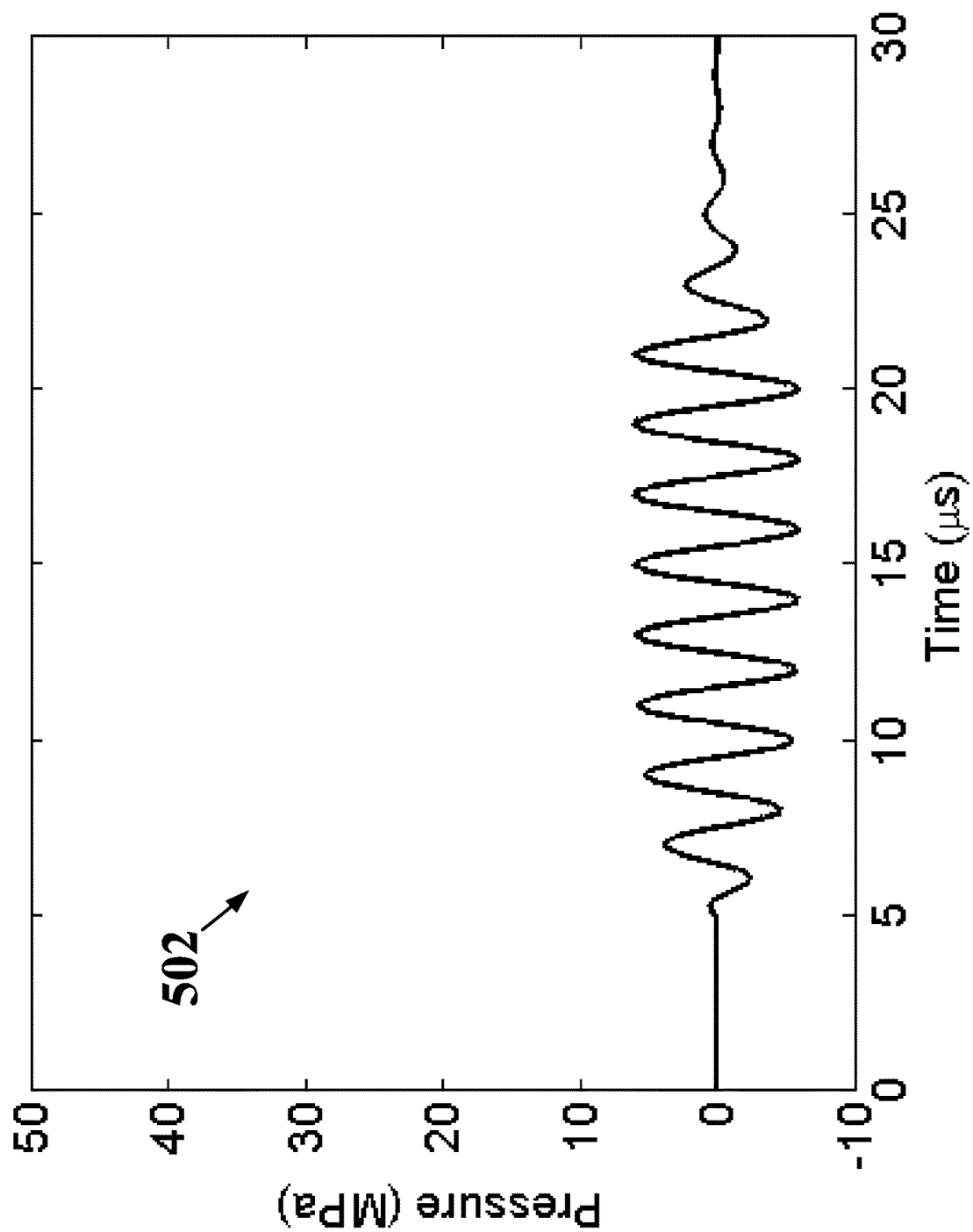
FIG. 5B shows aspects of burst in accordance with one or more example embodiments.

FIG. 5B shows aspects of burst in accordance with one or more example embodiments. In some embodiments, burst 502 may be produced, for example, in any of the manners described above in relation to FIGS. 1 through 5A. For example, properties of BWL waveform 500 may be determined using a mathematical software platform (e.g., MATLAB code), creating BWL waveform 502 in graphical space. As such, burst 502 may be sent to transducer 216 for producing BWL burst 502 to fragment or comminute an object. FIG. 5B may illustrate an example close-up view of burst 502. In some embodiments, burst 502 may, for example, take any of the forms described above in relation to FIG. 5A. In FIG. 5B, burst 502 may be measured by pressure (MPa) (or pressure amplitude) on the y-axis and time (μs) on the x-axis. In particular, burst 502 may range from −8 MPa to 8 MPa. Further, burst 502 may have a burst time of 20 μs (measured from 5 μs to 25 μson the x-axis).

Figure 5C:
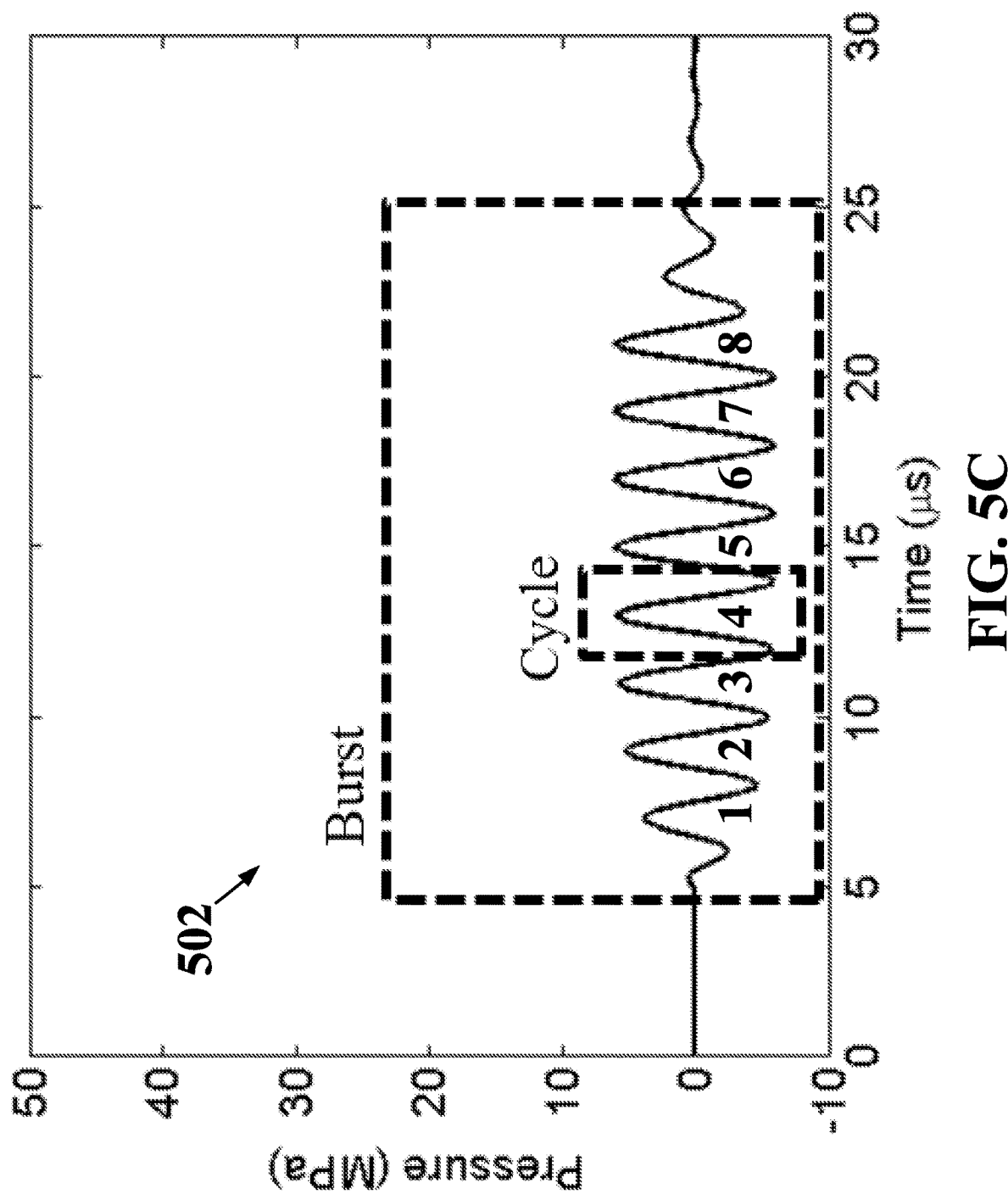
FIG. 5C shows aspects of a burst and multiple cycles in accordance with one or more example embodiments.

FIG. 5C shows aspects of a burst and multiple cycles in accordance with one or more example embodiments. As shown, burst 502 in FIG. 5C may be the same as burst 502 in FIG. 5B. Thus, burst 502 may be produced, for example, in any of the manners described above in relation to FIGS. 1 through 5B. Further, burst 502 in FIG. 5C may, for example, take any of the forms of bursts described above in relation to FIGS. 5A and 5B. As shown in FIG. 5C, the bigger dotted box around burst 502 may illustrate the burst time of 20 μs (measured from 5 μs to 25 μs on the x-axis). The areas on the left and right sides of the bigger dotted box may illustrate rest times. In addition, the smaller dotted box may illustrate cycle 4 of burst 502. As shown, there may be cycles 1 through cycle 8 in burst 502. With one cycle per 2 μs, the cycle frequency of cycles 1 through 8 may be 500 kHz.

Figure 6:
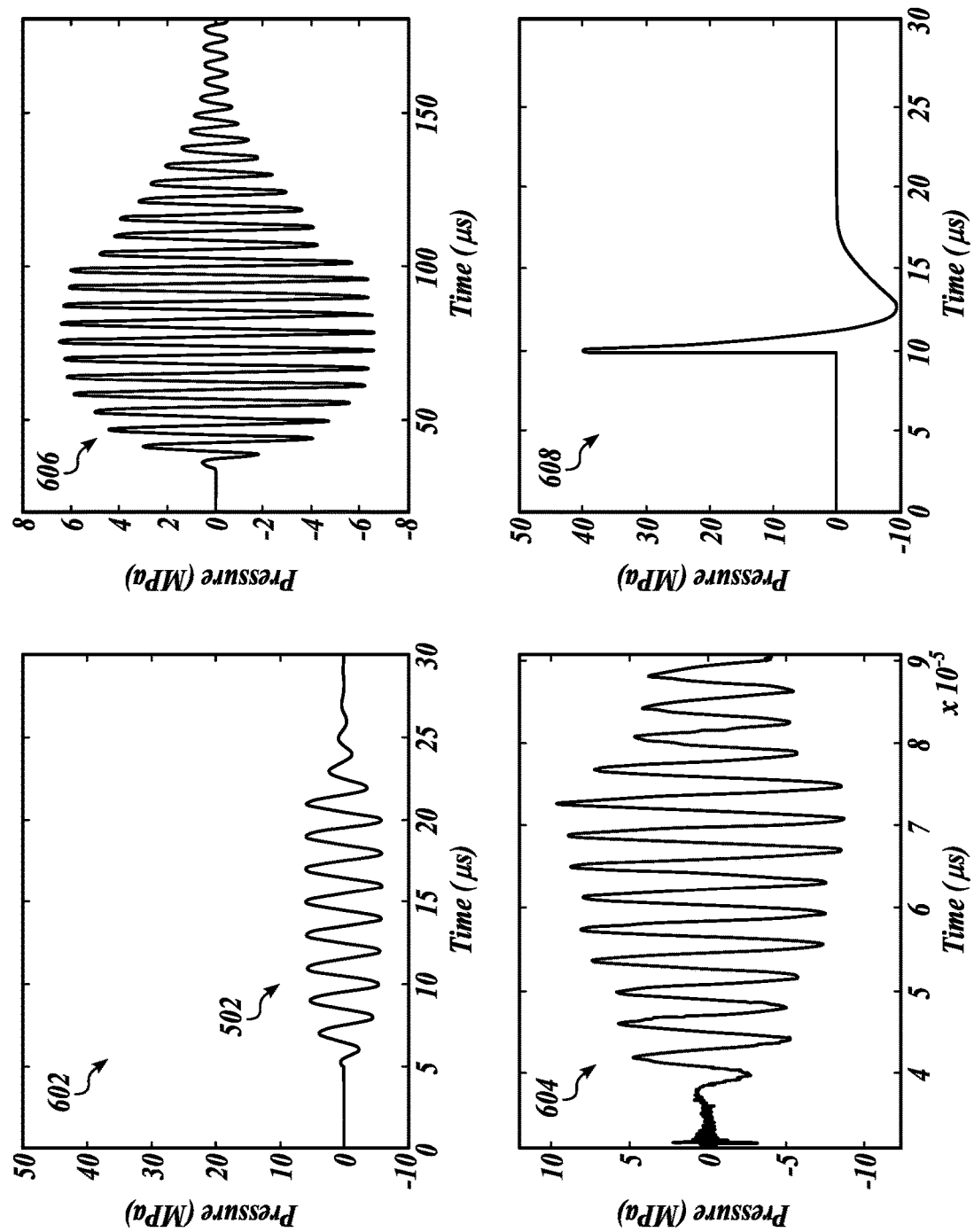
FIG. 6 shows aspects of multiple BWL waveforms in comparison to a shock wave lithotripsy waveform in accordance with one or more example embodiments.

FIG. 6 shows aspects of multiple BWL waveforms in comparison to a shock wave lithotripsy waveform in accordance with one or more example embodiments. In some embodiments, BWL waveforms 602, 604, and 606 may be produced, for example, in any of the manners described above in relation to FIGS. 1 through 4. For example, properties of BWL waveforms 602, 604, and 606 may be determined using a mathematical software platform (e.g., MATLAB code), creating BWL waveforms 602, 604, and 606 in graphical space. As such, BWL waveforms 602, 604, and 606 may be sent to transducer 216 for producing BWL waveforms 602, 604, and 606 to fragment or comminute object 220.

As shown, BWL waveform 602 includes burst 502. Further, burst 502 in FIG. 6 may be the same as burst 502 in FIG. 5C. Thus, burst 502 in FIG. 6 may, for example, take any of the forms of bursts described above in relation to FIGS. 5A through 5C. As shown, BWL waveform 604 may have varying pressure amplitudes for each cycle in a burst. In particular, the pressure amplitudes of the cycles may vary from −9 MPa to 10 MPa. Further, BWL 604 may have a burst time of more than 50 μs (approximately measured from 40 μs to 90 μs on the x-axis).

In addition, BWL waveform 606 may also have varying pressure amplitudes for each cycle in a burst. In particular, the pressure amplitudes of the cycles may vary from—7 MPa to 7 MPa. Further, BWL 606 may have a burst time of approximately 120 μs (approximately measured from 30 μs to 150 μs on the x-axis). Yet further, BWL wave 606 may have a ten cycles in its burst with a burst frequency of 200 Hz, for example. For an example comparison with BWL waveforms 602, 604, and 606, shockwave lithotripsy (SWL) waveform 608 is also illustrated in FIG. 6. As shown, SWL waveform 608 has a pressure amplitude from approximately −10 MPa to 40 MPa. It should be noted that such greater pressure amplitudes and one or more shapes of the SWL waveform 608 may cause cavitation of bodily tissue, possibly causing tissue injury to a subject.

Figure 7:
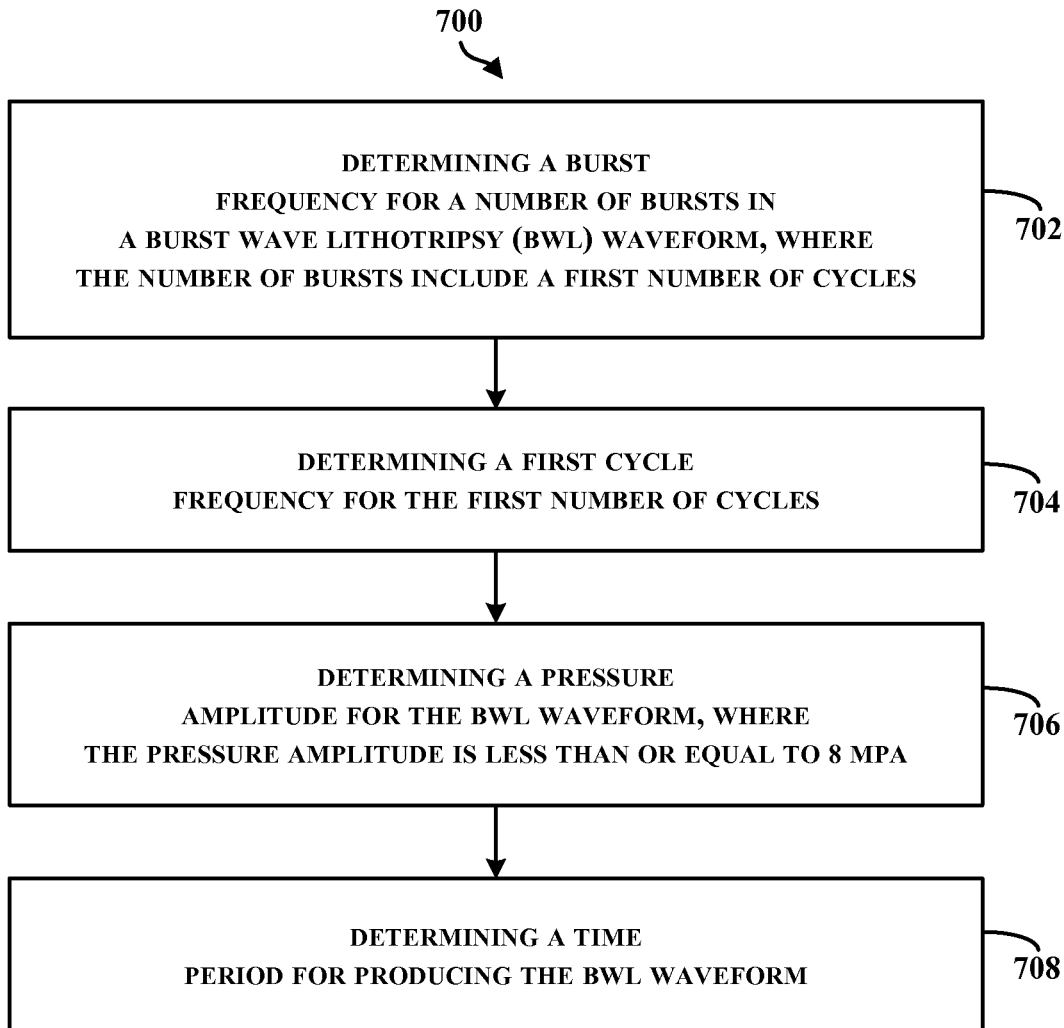
FIG. 7 shows a simplified flow chart to implement one or more example embodiments.

FIG. 7 shows a simplified flow chart to implement one or more example embodiments. For purposes of example and explanation, aspects of such example methods are described with reference to an example computing device. It should be understood, however, that the example methods described herein may apply just as well to any suitable computing device including, but not limited to, a portable computing device coupled with a transducer, a computing device integrated with a computer, a portable computing device integrated with a medical device, and/or another computing system, among other examples.

In FIG. 7, method 700 is described by way of example as being carried out by a computing device, possibly a computing device coupled to a transducer. For example, method 700 may be carried out by computing device 102 and transducer 216. Further, example methods, such as method 700, can be carried out by devices other than a computing device or can be carried out by sub-systems in a computing device. For instance, method 700 may be carried out by a computing device coupled with a graphical display, possibly for viewing characteristics of an object within a subject.

In some embodiments, various steps or sub-steps of method 700 may be carried out by network-access devices 102 through 108, network 110, and/or server 112. Further, various steps or sub-steps of method 700 may be carried out by processor 202, program instructions 206, program logic 208, network interface 210, input/output function 212, ADC 214, transducer 216, and amplifier 218. In some instances, steps of method 700 for determining properties of a BWL waveform may be carried out using a mathematical software platform (e.g., MATLAB code), creating the BWL waveform in graphical space. Thus, the BWL waveform may be sent to transducer 216 for producing BWL waveforms to fragment or comminute object 220.

As shown in FIG. 7, method 700 involves a method for producing a burst wave lithotripsy (BWL) waveform using a computing device. For example, a computing device coupled to a transducer may carry out functions to determined properties of a BWL waveform for producing the BWL waveform to fragment or comminute an object. At block 702, the computing device may determine a burst frequency for a number of bursts in a burst wave lithotripsy (BWL) waveform, where the number of bursts includes a first number of cycles. At block 704, the computing device may determine a first cycle frequency for the first number of cycles. At block 706, the computing device may determine a pressure amplitude for the BWL waveform, where the pressure amplitude may be less than or equal 8 MPa. At block 708, the computing device may determine a time period for producing the BWL waveform.

In some embodiments, the computing device may determine or control properties of the BWL waveform. In some clinical embodiments, an operator of the computing device may set properties of the BWL waveform before treating a subject with an object such as a kidney stone. In some instances, the operator may enter the properties of the BWL waveform in the computing device or a computer coupled to the computing device. As such, the computing device and/or the computer may create the BWL waveform and send the BWL waveform to an amplifier in the computing device. Further, the BWL waveform may be applied as a voltage to a transducer coupled to the computing device. Yet further, the transducer may be placed on the subject's skin and the BWL signal may be produced to fragment or comminute the kidney stone in the subject. It should be noted that one or more of the burst frequency, the first cycle frequency, the pressure amplitude, and the time period may be predetermined as a standard setting of the computing device. In some embodiments, such predetermined or standardized settings of the computing device may be defined for producing the BWL waveform for fragmenting or comminuting the stone. In some embodiments, the setting may be adjusted based on the position, size, shape, composition, and/or properties of the stone.

In some embodiments, the computing device may determine the position, size, shape, composition, and/or properties of an object. Further, in some embodiments, the computing device may be coupled to a computer that displays an image of the object (e.g., a kidney stone). In some instances, the transducer may be positioned to focus the BWL waveform with the stone and/or the BWL may be aligned with the stone. In some instances, the images of the kidney stone may be displayed in real-time as a video to determine whether the stone is fragmented and to what extent the stone is fragmented. Further, imaging the kidney stone may involve displaying one or more of fragments separated from the stone, the size or dimensions of the fragments separated from the stone, and the size or the dimensions of the fragmented stone. In addition, the images may provide an indication of cavitation of the tissue surrounding the stone or in the vicinity of the stone. As such, the imaging of the stone and the surrounding tissues may provide feedback signals to determine whether the BWL therapy should continue.

a. Determining a Burst Frequency

As noted for block 702 of FIG. 7, a computing device may carry out functions for determining a burst frequency for a number of bursts in a burst wave lithotripsy (BWL) waveform, where the number of bursts includes a first number of cycles. The burst frequency may be determined, for example, in any of the manners described above in relation to FIGS. 1 through 6. For example, as shown in FIG. 5A, a 5 kHz burst frequency may be determined for BWL waveform 500 to produce one burst for every 0.2 ms. Yet further, as noted, the number of bursts includes a number of cycles. The number of cycles may take, for example, any of the forms described above in relation to FIGS. 5A through 5C. For example, as shown in FIG. 5C, cycles 1 through 8 may be determined for burst 502.

In some embodiments, the burst frequency may be determined based on the burst time period and the rest time period of a BWL waveform. For example, referring back to FIG. 5A, the burst time period may be set to one one-hundredths of a second (0.01 seconds). In such instances, the burst frequency of 1 burst per one one-hundredths of a second would be a burst frequency of 100 Hz. Further, in some embodiments, a burst frequency range may be determined for a BWL waveform. For example, the burst frequency range may be from approximately 3 Hz to 1,000 Hz.

In some embodiments, different burst frequencies may be determined for producing a number of bursts in a BWL waveform. For example, in FIG. 5A, a first burst frequency of 100 Hz may be determined for producing bursts 501 through 503. Further, a second burst frequency of 200 Hz may be determined for producing bursts N-1 and N. As such, determining the first burst frequency and the second burst frequency may involve changing from the first burst frequency to the second burst frequency for producing BWL waveform 500.

In some embodiments, the burst frequency of a BWL waveform may be adjusted to fragment or comminute an object. For instance, in FIG. 5A, the burst time period appears to be longer than the rest time period. In some embodiments, the burst time period and/or the rest time period may be shortened or extended to produce a BWL waveform intended to fragment or comminute an object. In some embodiments, a particular burst frequency may be determined for fragmenting an object. For example, a burst frequency of 200 Hz may be used with an approximate pressure amplitude of 6.5 MPa for fragmenting an object. In such instances, the size of the fragments may vary between 0.1 to 1 mm. Further, using a lower burst frequency of 150 Hz with the approximate pressure amplitude of 6.5 MPa may, for example, result with larger fragments, possibly greater than 1 mm. As noted, the rest time period may be any time period in between bursts. In some instances, the rest time period may vary based on determining the burst frequency.

In some embodiments, different burst frequencies may be determined to produce a number of BWL waveforms. For example, referring back to FIG. 6, different burst frequencies may be set for BWL waveforms 602, 604, and 606. In particular, a burst frequency of about 4 kHz (approximately one burst per 250 µs) may be determined to produce BWL 602. Further, a burst frequency of about 11 kHz (approximately one burst per 90 µs) may be determined to produce BWL 604. Further, a burst frequency of about 6.7 kHz (approximately one burst per 130 µs) may be set to produce BWL 606. It should be noted that BWL waveforms 602, 604, and 606 may be produced to fragment or comminute a single object in a subject.

In some embodiments, the burst frequency may be adjusted based on the type of an object. It should be noted that different objects may have different properties or compositions affecting the strength of the object, possibly measured by a tensile strength of the object and/or the sound speed of the object. For example, a tensile strength of calcium oxalate monohydrate (COM) measured in megapascals (MPa) may vary from 3.1 MPa to 5.2 MPa. Further, a composite of struvite may have tensile strength that varies from 0.6 to 1.3 MPa. As such, in some embodiments, the burst frequency may be increased for fragmenting or comminuting objects with higher sound speeds such as calcium oxalate monohydrate (COM) and/or cystine. In some embodiments, the burst frequency may be decreased for fragmenting or comminuting objects with lower sound speeds such as struvite and/or calcium oxalate dihydrate. It should be noted that the type of the object may be determined, for example, using any of the manners described below in relation to FIGS. 10A, 10B, and 11.

It should be noted that the burst frequency may be determined by an operator of a computing device in an effort to fragment or comminute an object in a subject. For example, the operator may set the burst frequency based on an image of an object that the operator seeks to fragment or comminute. In some instances, the computing device may set the burst frequency based on one or more of the determined cycle frequency, the determined pressure amplitude, and the determined time period for producing the BWL waveform.

b. Determining a First Cycle Frequency

As noted for block 704 of FIG. 7, the computing device may carry out functions for determining a first cycle frequency for a first number of cycles. The first cycle frequency may be determined, for example, in any of the manners described above in relation to FIGS. 1 through 6. For example, as shown in FIG. 5C, a 500 kHz first cycle frequency may be determined for cycles 1 through 8 for producing one cycle for every 2 μs.

In some embodiments, a first cycle frequency may be determined for producing a first number of cycles and a second cycle frequency may be determined for producing a second number of cycles. For example, referring to the example above, a second cycle frequency, possibly different than the first cycle frequency of 500 kHz, may be determined for a second number of cycles 9 through 16 (not shown in FIG. 5C). In this example, determining the first cycle frequency and the second cycle frequency may involve changing from the first cycle frequency to the second cycle frequency between burst 502 to a subsequent burst. For additional examples, referring back to FIG. 5A, burst 501 may include a first number of cycles with a first cycle frequency of 200 kHz. Further, burst 502 may, for example, include a second number of cycles with a second cycle frequency of 500 kHz.

In some embodiments, the first cycle frequency may be determined to produce the first number of cycles to fragment an object, possibly separating a number of fragments from the object. Further, the second cycle frequency may be determined to produce the second number of cycles to further fragment the objects and the number of fragments separated from the object. In some instances, the first number of cycles may be used to break smaller stones free from plaque or tissue. Further, the second number of cycles may be used to fragment these smaller stones. Further, considering another scenario for FIG. 5C, cycles 1 through 4 may have a first cycle frequency of 200 kHz. In addition, cycles 5 through 8 may have a second cycle frequency of 500 kHz.

It should be noted that in this scenario, cycles 1 through 4 may be referred to as a first number of cycles and cycles 5 through 8 may be referred to as a second number of cycles. In this example, producing the first cycle frequency and the second cycle frequency may involve changing from the first cycle frequency to the second cycle frequency during a single burst 502.

In some embodiments, a cycle frequency range may be determined for a number of cycles. For example, referring back to Figure 5A, the first cycle frequency range of 100 kHz to 500 kHz may be determined for a first number of cycles in burst 501. Further, a second cycle frequency range may be determined for a second number of cycles in burst 502, possibly different than the first cycle frequency range. For instance, the second cycle frequency range may be determined to be 500 kHz to 1 MHz. As a general matter, a cycle frequency range may be from approximately 100 kHz to 1 MHz, among other possible ranges.

In some embodiments, the cycle frequency may be adjusted based on the type of the object. As noted, different objects may have different properties or compositions affecting the strength of the object, possibly measured by tensile strength of the object and/or the sound speed of the object. As such, in some embodiments, the cycle frequency may be increased for fragmenting or comminuting objects with higher sound speeds such as calcium oxalate monohydrate (COM) and/or cystine. In some embodiments, the cycle frequency may be decreased for fragmenting or comminuting objects with lower sound speeds such as struvite and/or calcium oxalate dihydrate. As noted, the type of the object may be determined, for example, using any of the manners described below in relation to FIGS. 10A, 10B, and 11. In some embodiments, the cycle frequency may be adjusted to fragment or comminute an object.

For example, a cycle frequency of 170 kHz may be used with an approximate pressure amplitude of 6.5 MPa for fragmenting an object. In such instances, the size of the fragments may, for example, vary between 2 to 4 mm. Further, using a lower cycle frequency of 100 kHz with the approximate pressure amplitude of 6.5 MPa may, for example, result in larger fragments possibly varying between 3.4 to 6.8 mm.

Figure 8:
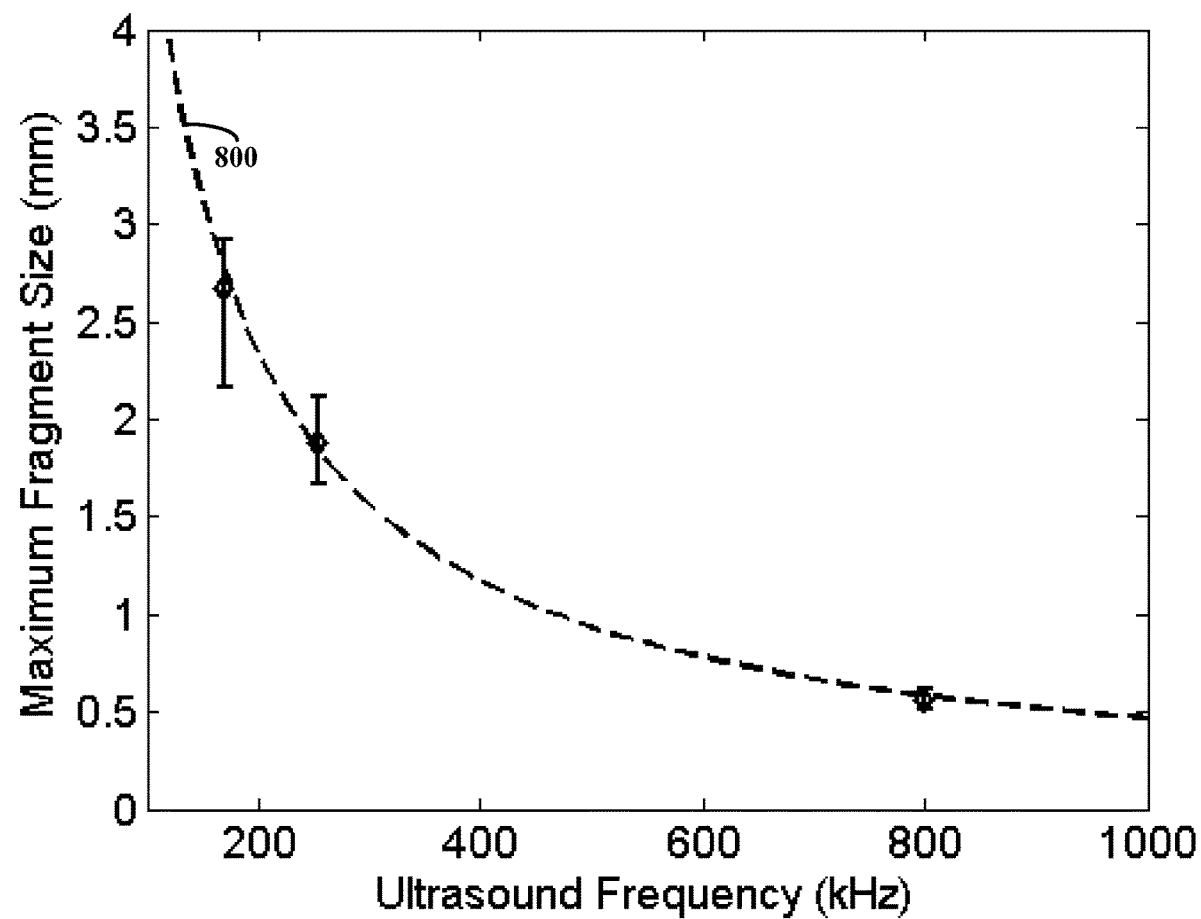
FIG. 8 shows aspects of fragmentation size based on cycle frequency in accordance with one or more embodiments.

In some embodiments, the cycle frequency may be determined for producing the BWL waveform in accordance with fragment sizes. FIG. 8 shows aspects of fragmentation size based on cycle frequency in accordance with one or more embodiments. The cycle frequencies (illustrated as "Ultrasound Frequency (kHz)") may correspond to cycle frequencies for producing BWL waveforms, for example, in any of the manners described above in relation to FIGS. 1 through 7. As shown in FIG. 8, the y-axis provides maximum fragment sizes and the x-axis provides various cycle frequencies of a BWL waveform. It should be understood that maximum fragment sizes may refer to the maximum sizes of fragments separated from an object caused by the BWL waveform interacting with the object. In some instances, the maximum fragment size may be referred to as a target fragment size.

As shown in FIG. 8, a 200 kHz cycle frequency may be used for producing a BWL waveform to separate fragments from an object. In such instances, the fragments may have a 2.5 to 3 mm maximum fragment size. Further, a cycle frequency from approximately 220 kHz to 300 kHz may be used for producing a BWL waveform to separate fragments from an object. In such instances, the fragments may have a 1.5 to 2.2 mm maximum fragment size. Yet further, an 800 kHz frequency may be used for producing a BWL waveform to separate fragments from an object. In such instances, the fragments may have a 0.5 to 1 mm maximum fragment size.

Further, as illustrated in FIG. 8, a cycle frequency may be determined to produce a BWL waveform based on a target fragment size. As shown, curve 800 may correspond to an expression:

$$D = \frac{0.47}{f(\text{MHz})}(\text{mm}).$$

Further, curve 800 may also be expressed as the expression:

$$f(\text{MHz}) = \frac{0.47}{D(\text{mm})}.$$

In particular, f(MHz) is the cycle frequency in megahertz and D is the target fragment size in millimeters. In some embodiments, the target fragment size may be used to determine the cycle frequency used to produce a BWL waveform for fragmenting or comminuting an object. For example, the target fragment size may be an input to determine the cycle frequency for producing the BWL waveform to fragment an object in a subject.

It should be noted that the cycle frequency may be determined by an operator of a computing device in an effort to fragment or comminute an object in a subject. For example, the operator may set the cycle frequency based on an image of an object. In some instances, the computing device may set the cycle frequency based on one or more of the determined burst frequency, the determined pressure amplitude, and the determined time period for producing the BWL waveform.

c. Determining a Pressure Amplitude

As noted for block 706 of FIG. 7, the computing device may carry out functions for determining a pressure amplitude for the BWL waveform, where the pressure amplitude may be less than or equal to 8 MPa. The pressure amplitude may be determined, for example, in any of the manners described above in relation to FIGS. 1 through 8. In some instances, BWL waveforms may include peak positive pressures (P+) and peak negative pressures (P−). For example, as shown in burst 502 of FIGS. 5B, 5C, and 6, varying pressure amplitudes from −8 MPa to 8 MPa may be determined for a BWL waveform. Further, as shown for BWL waveform 604 of FIG. 6, varying pressure amplitudes from −9 MPa to 10 MPa may be determined. Further, as shown for BWL waveform 606, varying pressure amplitudes from −7 MPa to 7 MPa may be determined, among other possibilities.

In some embodiments, the pressure amplitudes may be determined to be lower than those of other forms of lithotripsy. For example, referring back to FIG. 6, pressure amplitudes may be determined for producing BWL waveforms 602, 604, and 606. As such, the pressure amplitudes for BWL waveforms 602, 604, and 606 are far lower than the pressure amplitude of SWL waveform 608. As such, pressure amplitudes may be determined for producing BWL waveforms 602, 604, and 606 such that energy levels may be high enough to fragment or comminute an object, but not high enough to cause cavitation, thermal damage, and/or mechanical damage to surrounding tissues.

In some embodiments, different pressure amplitudes may be determined for each of different BWL waveforms or bursts. For example, as shown in FIG. 6, consider a scenario of setting different pressure amplitudes for producing BWL waveforms 602, 604, and 606. In particular, the pressure amplitude of BWL waveform 602 may range from approximately −8 to 8 MPa. Further, BWL waveform 604 may have varying pressure amplitudes from approximately −9 to 10 MPa. Yet further, BWL waveform 606 may also have varying pressure amplitudes from approximately −7 to 7 MPa. In some embodiments, pressure amplitudes may be determined to produce BWL waveforms 602, 604, and 606 to fragment a single object in a subject.

In some embodiments, the pressure amplitude may be adjusted based on the type of the object being fragmented or comminuted. As noted, different objects may have different properties or compositions affecting the strength of the object, possibly measured by tensile strength and/or the sound speed of the object. For example, COM may have a tensile strength from 3.1 to 5.2 MPa. Yet further, a composite of struvite may have tensile strength that varies from 0.6 to 1.3 MPa. As such, in some embodiments, the pressure amplitude may be increased for fragmenting or comminuting COM. In some embodiments, the pressure amplitude may be decreased for fragmenting or comminuting struvite. As noted, the type of the object may be determined, for example, using any of the manners described below in relation to FIGS. 10A, 10B, and 11.

In some embodiments, the pressure amplitude may be determined for a time period for producing the BWL waveform. Further, in some embodiments, the pressure amplitude may be determined for a time period to fragment or comminute an object. For example, setting the pressure amplitude to 6.5 MPa for a BWL waveform may initiate a fracture in an object in approximately 5 minutes. Yet further, setting the pressure amplitude to 6.5 MPa for the BWL waveform may comminute the object in approximately 9.7 minutes. In some embodiments, the 6.5 MPa pressure amplitude may be used to comminute many types of objects including uric acid, struvite, COM, and/or cystine.

It should be noted that the pressure amplitude may be determined by an operator of a computing device in an effort to fragment or comminute an object in a subject. For example, the operator may set the pressure amplitude based on an image of an object. In some instances, the computing device may set the pressure amplitude based on one or more of the determined burst frequency, the determined cycle frequency, and the determined time period for producing the BWL waveform.

d. Determining a Time Period for Producing the BWL Waveform

As noted for block 708 of FIG. 7, the computing device may carry out functions for determining a time period for producing the BWL waveform. In some embodiments, the time period for producing the BWL waveform may be determined based on a total time period of burst time periods and rest time periods. For example, the time period for producing the BWL waveform may be determined, for example, in any of the manners described above in relation to FIGS. 1 through 6. As shown in FIG. 5A, a burst time period and a rest time period is determined for producing bursts in BWL waveform 500. In particular, burst time periods may be determined for bursts 501, 502, 503, N-1, and N, and further, rest time periods may be determined in between these bursts. In some embodiments, the burst time periods and/or the rest time periods may range from approximately 1 µs to 1 ms. As such, combining the burst time periods and the rest time periods may amount to a total time period for producing BWL waveform 500. In some instances, the time period for producing BWL waveform 500 may range from approximately 4 seconds to 21 minutes. As noted, the rest time period may be any time period in between bursts. Further, the rest time period may vary with the burst frequency, for example.

In some embodiments, the time period for producing the BWL waveform may be determined to fragment or comminute an object. For example, a time period of approximately five minutes may be determined for producing a BWL waveform to fracture or initiate a fracture of an object. In this example, a cycle frequency of 170 kHz may be used to fracture the object during the approximate five minute time period. In another example, a time period ranging from approximately 6.9 to 11.5 minutes may be determined for comminuting an object. In particular, this time period may be set for a BWL waveform with a 170 kHz cycle frequency and a pressure amplitude 6.5 MPa.

Figure 9:
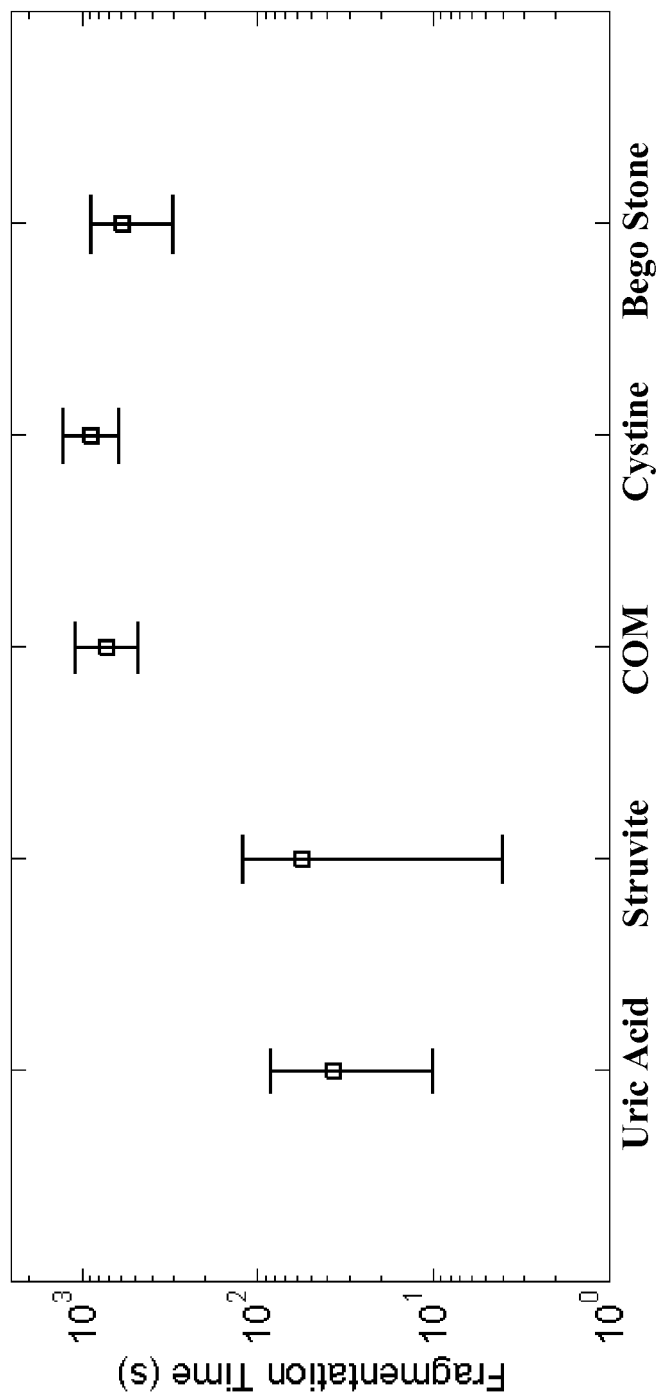
FIG. 9 shows aspects of fragmentation times in accordance with one or more embodiments.

In some embodiments, the time period for producing the BWL waveform may be a time period for fragmenting or comminuting an object. FIG. 9 shows aspects of fragmentation times in accordance with one or more embodiments. The fragmentation times may correspond to time periods for producing BWL waveforms, for example, in any of the manners described above in relation to FIGS. 1 through 7. As shown in FIG. 9, the y-axis provides time periods for fragmenting objects and the x-axis provides various types of objects that may be fragmented. Thus, in some instances, the time period for producing the BWL waveform may be determined based on type of object.

For example, a time period ranging from approximately 10 to 100 seconds may be determined for fragmenting or comminuting an object made of uric acid. Further, a time period ranging from approximately 1 to 100 seconds may be determined for fragmenting or comminuting an object made of struvite. Yet further, a time period ranging from approximately 15 to 21 minutes may be determined for fragmenting or comminuting an object made of COM or cystine. In addition, a time period ranging from approximately 12 to 18 minutes may be determined for fragmenting or comminuting an artificial object such as a bego stone. In some embodiments, an estimated comminution rate of approximately 12 to 520 mm$^3$ per minute may be determined for producing the BWL waveform.

In some embodiments, the time period for producing the BWL waveform may be determined based on the number of bursts required for fragmenting or comminuting an object. For example, it may be estimated that 100 bursts are required for fragmenting a given object.

Thus, using a 10 Hz burst frequency, a time period of 10 second may be required for producing the BWL waveform to fragment the given object. In some embodiments, the time period for producing the BWL waveform may be determined based on the number of cycles required for fragmenting or comminuting an object. For example, referring back to FIG. 5C, consider a scenario such that 8×10$^6$ cycles are required or estimated to comminute a given object. In this example, further consider that burst 502 has a cycle frequency of one cycle per 2 µs or 500 kHz. As such, a time period of 16 seconds may be determined for producing a BWL waveform for comminuting the object.

In some embodiments, the time period for producing the BWL waveform may be determined based on the type of object. As noted, different objects may have different properties or compositions affecting the strength of the object, possibly measured by tensile strength of the object and/or the sound speed of the object. As noted, the type of the object may be determined, for example, using any of the manners described below in relation to FIGS. 10A, 10B, and 11. Further, in some embodiments, the time period for producing the BWL waveform may be determined based on a size or a dimension of an object. Yet further, the time period for producing the BWL waveform may be determined based on the cycle frequency. For example, a time period of 2 minutes may be determined for fragmenting or comminuting a 1.5 mm×8 mm struvite stone using a 175 kHz cycle frequency. Further, a time period of 15 minutes may be determined for fragmenting or comminuting an 8 mm×6 mm COM stone using a 175 kHz cycle frequency. Yet further, a time period of 10 minutes may be determined for fragmenting or comminuting an 11 mm×6 mm artificial object such as a bego stone using a 175 kHz cycle frequency.

It should be noted, that the time period for producing a BWL waveform may be a subset of a treatment time period. For example, the treatment time period may be the total time that a subject is exposed to a BWL waveform. Further, in some instances, the treatment time period may start from the time the transducer is first placed on the subject's skin and may end at the time the transducer is taken off of the subject after producing the BWL waveform. In such instances, the treatment time period may range from approximately 1 second to 1 hour.

It should be noted that the time period for producing a BWL waveform may be determined by an operator of a computing device in an effort to fragment or comminute an object in a subject. For example, the operator may set the time period based on an image of an object. In some instances, the computing device may set the time period based on one or more of the determined burst frequency, the determined cycle frequency, and the determined pressure amplitude for producing the BWL waveform.

e. Additional Examples for Producing a BWL waveform

As noted, method 700 involves a method for producing a burst wave lithotripsy (BWL) waveform using a computing device, such as computing device 102 as described in relation to FIGS. 1 through 9.

Figure 10A:
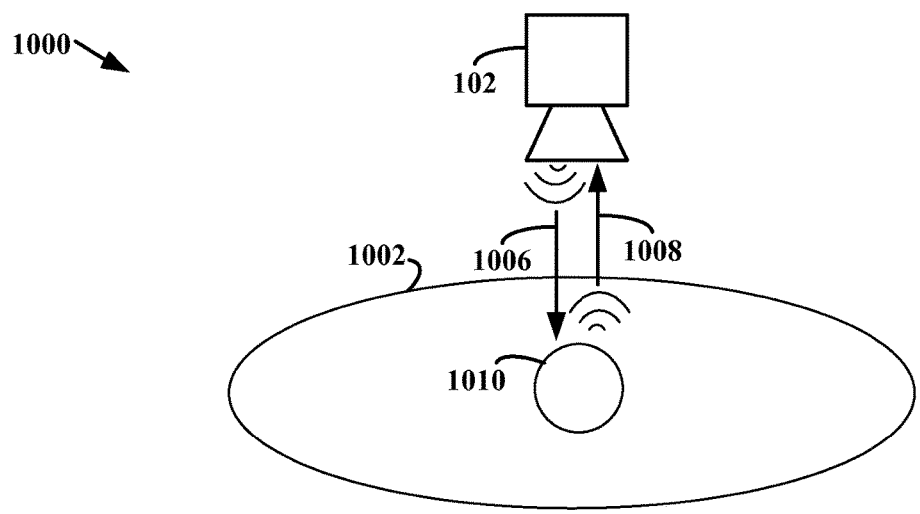
FIG. 10A shows aspects of a computing device to implement one or more example embodiments.
Figure 10B:
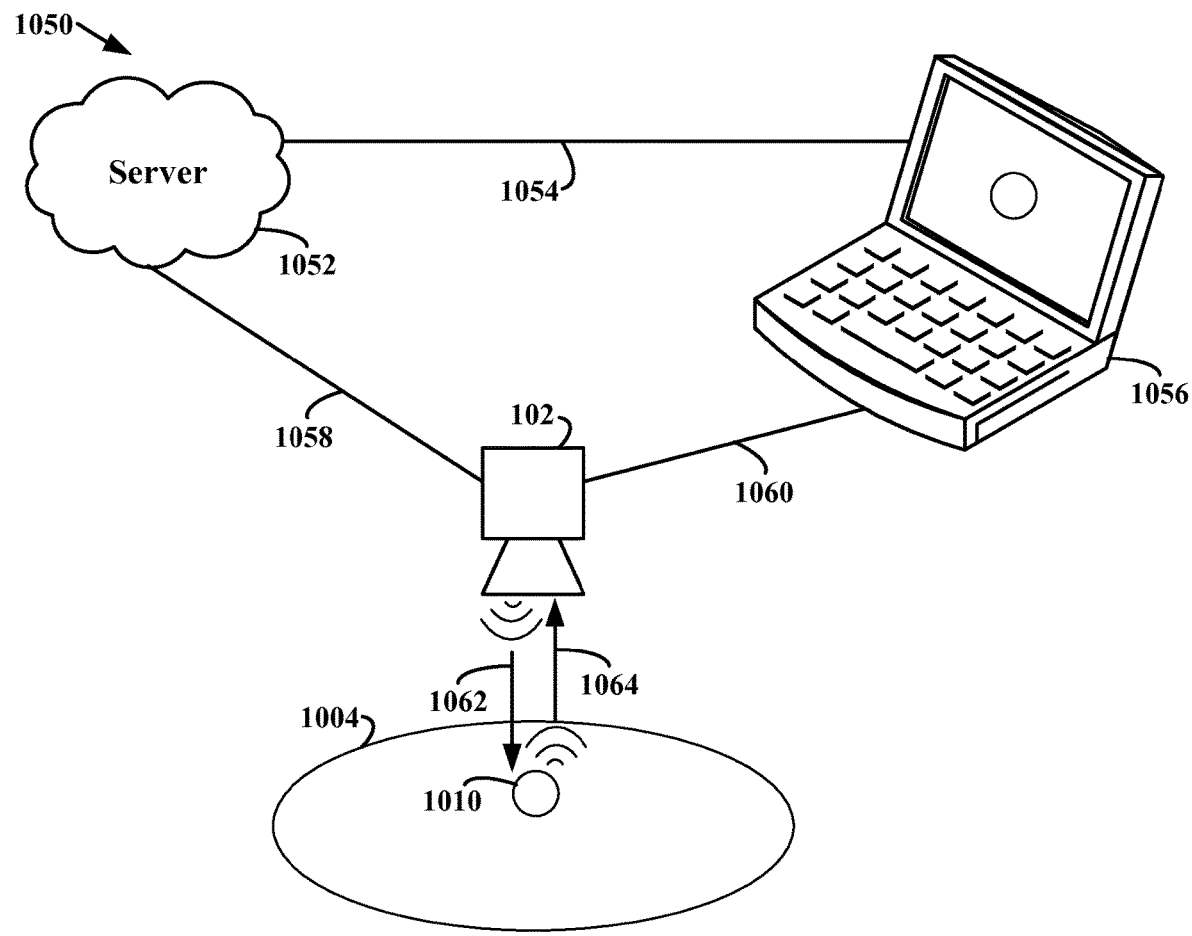
FIG. 10B shows additional aspects of a computing device to implement one or more example embodiments.

FIGS. 10A and 10B show aspects of a computing device to implement one or more example embodiments. More particularly, FIGS. 10A and 10B depict aspects of a computing device configured to carry out the methods, processes, and/or functions of FIG. 7 for producing a BWL waveform to fragment or comminute an object. Further, computing device 102, as shown, is an example computing device configured to produce the BWL waveform. In some embodiments, computing device 102 may produce imaging signals, for example, in addition to any of the steps or sub-steps in relation to FIGS. 1 through 9. For example, transducer 216, as described in relation to FIGS. 1 through 2B, may also produce imaging signals, ultrasound signals, B-mode pulses, and/or Doppler pulses, among other possibilities. Various respective features, characteristics, and/or functionality of the computing devices depicted in FIGS. 10A and 10B are discussed further below with respect to the example methods described herein.

In FIG. 10A, scenario 1000 provides a computing device 102 that may be positioned on the surface of medium 1002, near medium 1002, and/or possibly adjacent to or within the proximity of medium 1002, among other possibilities. Medium 1002 may be an open or a closed medium. For example, medium 1002 may be an open medium with a liquid, a gas, and/or a combination of liquids, gases, and solids. In some instances, medium 1002 may be a closed medium with a surface enclosing a liquid, a gas, a solid, and/or a combination of such elements. In some instances, medium 1002 may located within a subject or a living mammal. For example, medium 1002 may be an organ of a subject or a living mammal.

Computing device 102 in FIG. 10A may be understood to be computing device 102 described above in relation to FIGS. 1 through 2B. As such, computing device 102 may be configured to communicate with other computing devices. As illustrated in FIG. 10A, computing device 102 may produce imaging signals in a direction 1006 toward medium 1002 and object 1010. In some instances, computing device 102 may produce imaging signals that penetrate the surface or skin of medium 1002 and reflect off of object 1010. The reflected pulses (e.g., feedback signals) may return in a direction 1008 toward computing device 102 so as to be received by computing device 102. By analyzing the feedback signals, computing device 102 may identify object 1010 and characteristics of object 1010. For example, computing device 102 may identify the position, size, shape, composition, and/or properties of object 1010. In some instances, computing device 102 may identify whether object 1010 is fragmented or comminuted.

In some embodiments, medium 1002 may be part of a subject's body or a subject's organ encompassing object 1010. Further, object 1010 may be a kidney stone of any size. For example, object 1010 may be 1 to 15 mm in diameter and medium 1002 may be a kidney. In some embodiments, object 1010 may be a urinary tract stone, a kidney stone, a ureter stone or a ureteral stone, a bladder stone, a urethra stone or a urethral stone, a prostate stone or a prostatic stone, a salivary stone, a gallbladder stone, a gall stone, a bile duct or a stone in the bile duct, a blood clot, blood, mucous, stool, cerumen, bodily tissue, a calcification, a calcified plaque, Randall's plaque, an atherosclerotic plaque, uric acid, struvite, calcium oxalate monohydrate (COM), cystine, a tonsil stone, an artificial object, and an object introduced inside the subject (e.g., a bullet from a handgun, a catheter, and/or a stent), among other possibilities. In some instances, object 1010 may be a uretero-pelvic junction stone with a diameter of 2 cm or more. Yet further, in some instances, object 1010 maybe a mass or a buildup of minerals, such as a concretion, for example. Other examples of mediums and objects may exist.

FIG. 10B depicts additional aspects of a computing device in accordance with one or more example embodiments. In FIG. 10B, scenario 1050 provides a computing device 102 that may be positioned on the surface of medium 1004, near medium 1004, and/or possibly adjacent to or within the proximity of medium 1004, among other possibilities. In some instances, computing device 102 in FIG. 10B may be similar to computing device 102 in FIGS. 1 through 2B. In FIG. 10B, medium 1004 may be a subject's body (i.e., a human body), a mammal's body, or the body of some other living animal. As a general matter, object 1010 in FIG. 10 may be similar to object 1010 in FIG. 10A. In some instances, object 1010 may be a kidney stone that is approximately 5 to 12 mm in diameter.

It should be noted that although object 1010 in FIGS. 10A and 10B appears to be circular or spherical in form for illustrative purposes, other possibilities may also exist. As a general matter, object 1010 may take various other forms, shapes, and/or sizes. For example, in a scenario such that object 1010 is a kidney stone, the accumulation of minerals and salts that forms object 1010 may result in an asymmetrical structure of object 1010.

As illustrated in FIG. 10B, computing device 102 may produce imaging signals in a direction 1062 toward medium 1004 and object 1010. In some instances, computing device 102 may produce imaging signals that penetrate the surface or skin of medium 1004 and reflect off of object 1010. The reflected pulses or feedback signals may return in a direction 1064 toward computing device 102 and received by computing device 102. By analyzing the feedback signals, computing device 102 may identify object 1010 and characteristics of object 1010. For example, computing device 102 may identify the position, size, shape, composition, and/or properties of object 1010. In some instances, computing device 102 may identify whether object 1010 is fragmented or comminuted.

Further, as illustrated in FIG. 10B, computing device 102 may communicate with computer 1056 to display object 1010. Further, computer 1056 may display data indicative of the position (e.g., coordinates of object 1010 in a three-dimensional space), size, shape, composition, and/or properties of object 1010, including whether object 1010 is fragmented or comminuted. Further, computer may display data indicative of the material or tissues surrounding object 1010, such as the tissue of medium 1004 in the vicinity of object 1010, among other possibilities. As such, computer 1056 may provide information (e.g., a harmonic image) identifying object 1010 and characteristics of object 1010 in medium 1004. Further, computer 1056 may include a speaker to generate an audible sound corresponding to one or more feedback signals, possibly indicative of object 1070 being fragmented or comminuted.

It should be noted that computing device 102 and/or computer 1056 may be configured to receive inputs from a user. For example, computing device 102 and/or computer 1056 may include and/or be coupled to a human-interface device such as a keyboard, a mouse, a touch screen, a sensor, and/or any other device that is capable of receiving input. As such, computing device 102 and/or computer 1056 may receive inputs from a user to identify, fragment, and/or comminute object 1010. The inputs may include data corresponding to optical data from an optical mouse, alphanumeric data from a keyboard, capacitive data from a touchscreen, and/or motion data from a motion sensor, among other possibilities.

In some embodiments, producing a BWL waveform to fragment or comminute an object may involve analyzing an image of the object. To provide an image of the object, computing device 102 may enter various modes as described herein. As a general matter, B-mode and Doppler mode may be utilized for producing imaging signals and receiving feedback signals to image an object. In addition, computing device 102 may enter one or more other modes to produce imaging signals to identify characteristics of an object. Further, a computing device may enter fragment mode to produce BWL waveforms to fragment or comminute an object. In some instances, the fragment mode may initiate ultrasound waves or acoustic radiation forces that result from the transfer of acoustic wave momentum to an absorbing or reflecting object.

For example, B-mode ultrasound may be used to produce an image of object 1010 in FIGS. 10A and 10B. In some instances, radio frequency signals (e.g., non-beam formed signals) may be received for adjusting energy delivery and timing. In other instances, Doppler mode imaging signals may be used to generate an image of object 1010, among other possibilities. As further described herein, various modes may be employed to produce various types of signals and waveforms. It should be noted that B-mode ultrasound may be employed by producing imaging signals and receiving feedback signals, possibly as illustrated in FIGS. 10A and 10B.

In some embodiments, feedback signals may be analyzed to determine position data of object 1010. For example, phase delays of the feedback signals may be calculated to determine coordinates of a position of object 1010. Further, such calculations may also determine coordinates of a distance between computing device 102 and object 1010. It should be noted that distances between object 1010 and tissues in the vicinity of or surrounding object 1010 may also be determined. In addition, such calculations may also determine characteristics of object 1010 such as the size, shape, and/or dimensions of object 1010. In some instances, such characteristics may be used to determine aspects of imaging signals configured to adjust properties of a BWL waveform (e.g., beam width) to produce to fragment or comminute an object.

It should be noted that feedback signals may include various other signals for identifying characteristics of the object. For example, feedback signals may also include signals or data from various medical imaging technologies to identify characteristics of the object. In some instances, feedback signals may include signals from medical imaging devices and/or machines used to determine whether the object is fragmented or comminuted. For instance, x-rays, computed tomography, computed axial tomography, magnetic resonance imaging (MM) data, digital geometric processing, and/or other medical imaging procedures may provide feedback signals for identifying characteristics of the object. Yet further, feedback signals may include a synchronization or a combination of data from other modalities that may or may not use contrast-enhancement type material. Other possibilities may also exist.

Figure 11:
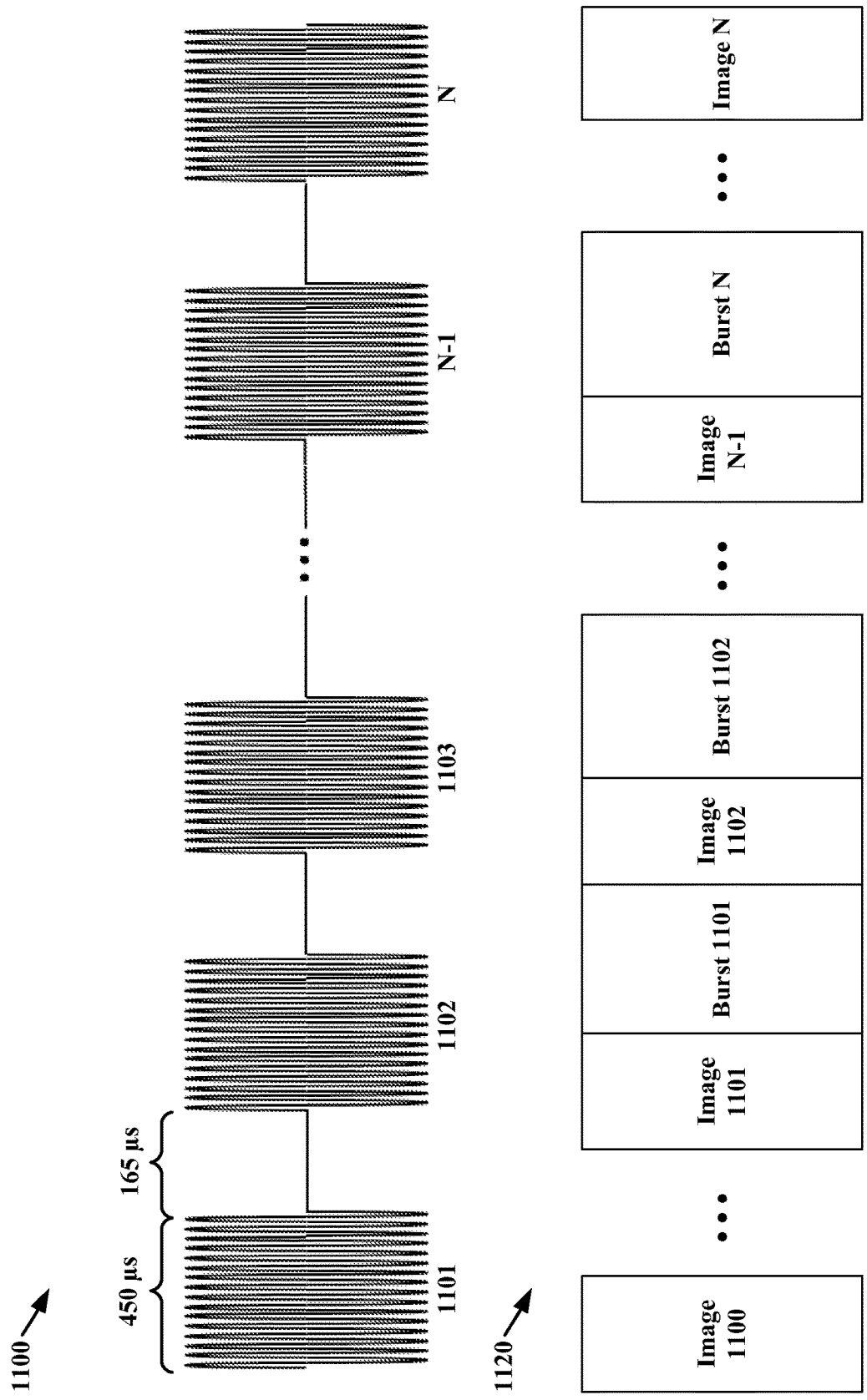
FIG. 11 shows aspects of producing a BWL waveform in accordance with one or more example embodiments.

In some embodiments, feedback signals may be received intermittently. In particular, feedback signals may be received intermittently by a computing device that produces BWL waveforms. FIG. 11 shows aspects of producing a BWL waveform in accordance with one or more example embodiments. As illustrated in FIG. 11, BWL waveform 1100 includes N bursts, bursts 1101, 1102, 1103, N-1, and N. Further, each burst includes a number of cycles. Yet further, BWL signal 1100 may include a burst time period of 450 microseconds followed by a rest time period of 165 microseconds, providing a 73% duty cycle. In some instances, BWL waveform 1100 may include a total burst duration of 50 milliseconds. As shown, BWL waveform 1100 may be the same or substantially similar to Figure SA. In some instances, BWL waveform 1100 may push or reposition an object and the burst time period may be adjusted to fragment or comminute the stone.

As shown, scenario 1120 includes an image 1100, possibly identifying an object and the position of the object within a subject. Further, image 1101 may identify characteristics of the object. As such, burst 1101 may be produced to fragment the object. In some instances, burst 1101 may also reposition the object from a first position to a second position within the subject. As such, image 1102 may illustrate the object in the second position within the subject. In addition, burst 1102 may fragment the object further and possibly reposition the object from the second position to a third position, and so on until image N-1 and burst N. In some instances, burst N may comminute the object and image N may illustrate various fragments of the object. In some embodiments, feedback signals may provide information for producing BWL waveforms. For example, the feedback signals used to display image 1101 and provide information for determining properties of BWL waveform 1100. For example, image 1101 may provide characteristics of the object such that burst 1101 may be configured and/or tailored to fragment or comminute the object.

In particular, image 1101 may provide characteristics including the composition, size, dimensions, shape or form of the object, and/or the material or tissue surrounding the object, among other possibilities. In addition, the beam width of any one of bursts 1101 through N may be adjusted accordingly to fragment or comminute the stone. Yet further, bursts 1101 through N may be programed and directed to the object by lateral dithering of bursts. Other possibilities may also exist.

It should be noted that scenario 1120 may be modified based on various factors. In particular, feedback signals may be received intermittently with producing bursts of the BWL waveform 1100 in various ways. For example, a pause between producing bursts of the BWL waveform 1100 may be extended to prevent overheating of the transducer (e.g., transducer 216 in FIGS. 2A through 2B) used to produce the BWL waveform 1100. In some instances, a thermocouple, a digital thermometer, and/or another temperature sensing device may be coupled with the transducer to monitor the temperature of the transducer. Further, temperature readings of the transducer may be used to adjust scenario 1120 for producing bursts of the BWL waveform 1120. For instance, as the temperature of the transducer increases, the transducer may initiate more pauses in between bursts to reduce the temperature. In other instances, the transducer may initiate a cooling mechanism to lower the temperature of the transducer. Other possibilities may also be implemented.

As noted, feedback signals may include a synchronization or a combination of data from other modalities that may or may not use contrast-enhancement type material. In some instances, feedback signals may be used to produce BWL waveforms in an automated process. As such, feedback signals may be used to provide a map of the object to various areas in the subject's body.

Figure 12:
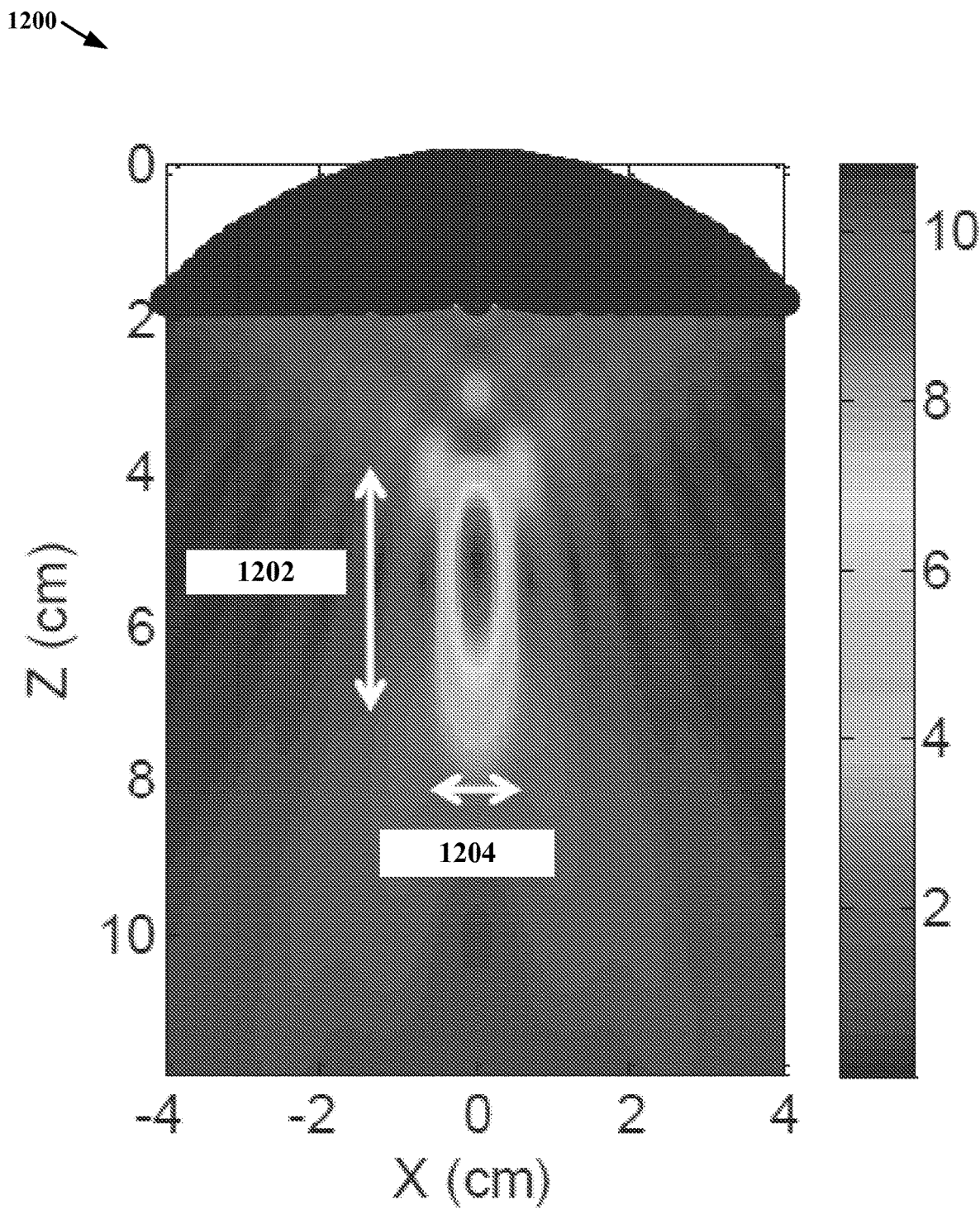
FIG. 12 shows aspects of a beam width in accordance with one or more example embodiments.

In some embodiments, a beam width of a BWL waveform may be determined for producing the BWL waveform. FIG. 12 shows aspects of a beam width in accordance with one or more example embodiments. Aspects of the beam width may be determined, for example, in any manner described above in relation to FIGS. 1 through 11. For example, the beam width may be determined in addition to the steps and/or sub-steps for determining properties of a BWL waveform as described above in relation to FIG. 7.

As shown in FIG. 12, scenario 1200 illustrates an example beam width map with a beam width of a BWL waveform measured in the z-dimension and the x-dimension. In scenario 1200, a beam width 1202 in the z-dimension and a beam width 1204 in the x-dimension are illustrated. In some embodiments, beam width 1202 may be approximately 30 mm and beam width 1204 may be approximately 7.6 mm. However, it should be noted that as a general matter, beam width 1202 and beam width 1204 may range from approximately 0.5 to 100 mm. As such, a broadly focused beam, a focused beam, or a unfocused beam may be determined to produce the BWL waveform for fragmenting or comminuting an object.

In some embodiments, a beam width of a BWL waveform may be adjusted based on the properties of an object. For example, one or more feedback signals may be received as described above in relation to FIGS. 10A and 10B, possibly providing a visual indication illustrating that the object has one or more surfaces. As such, properties of a BWL waveform may be determined to produce the BWL waveform with a broadly focused beam. For example, in FIG. 12, beam width 1202 and/or beam width 1204 may be adjusted such that the BWL waveform is produced or applied around the one or more surfaces of the object. In particular, beam width 1202 and beam width 1204 may be broader than the object, possibly to hold the object in place while the BWL waveform fragments or comminutes the object.

In some instances, beam widths may be adjusted to be larger than an object. For example, beam width 1202 and beam width 1204 may be adjusted to be approximately 15% to 40% larger than the object in an effort to maximize the energy applied to the stone. In some instances, the energy applied to the stone may be maximized while avoiding cavitation to tissues surrounding the stone. In particular, the BWL waveform may be produced to avoid cavitation and cavitation clouds. However, it should be noted that cavitation bubbles may appear on the surfaces of the object.

In some embodiments, pushing ultrasound may be produced to move an object.

In some embodiments, the pushing ultrasound may be produced separately or in combination with producing a BWL waveform to fragment or comminute the object. In some instances, pushing ultrasound may move an object while the BWL waveform is produced to fragment or comminute the object. In particular, the object may move and the BWL waveform may be produced around one or more surfaces of the moving object. Further, the object may rotate or turn and the BWL waveform may be produced over the surfaces of the object. As such, the object may fragment or comminute. In some embodiments, BWL waveforms may be used in addition to extracorporeal shockwave lithotripsy (SWL), histotripsy, high-intensity focused ultrasound, ultrasonic propulsion, ureteroscopic lithotripsy, and/or percutaneous nephrolithotomy to fragment objects.

4. Additional Implementations, Applications, and Examples

Abstract

Purpose: We have developed a new method of lithotripsy that uses short, broadly focused bursts of ultrasound rather than shock waves to fragment stones. This study investigated the characteristics of stone comminution by burst wave lithotripsy in vitro.

Materials and Methods: Artificial and natural stones (mean 8.2±3.0 mm, range 5-15 mm) were treated with ultrasound bursts using a focused ultrasound transducer in a water bath. Stones were exposed to bursts with focal pressure amplitude ≤6.5 MPa at 200 Hz burst repetition rate until the stones were completely fragmented. Ultrasound frequencies of 170 kHz, 285 kHz, and 800 kHz were applied. The time to achieve fragmentation for each stone type was recorded, and fragment size distribution was measured by sieving.

Results: Stones exposed to ultrasound bursts were fragmented at focal pressure amplitudes 2.8 MPa at 170 kHz. Fractures appeared along the stone surface, resulting in fragments separating at the surface nearest to the transducer until the stone was disintegrated. All natural and artificial stones were fragmented at the highest focal pressure of 6.5 MPa with treatment durations between a mean of 36 seconds for uric acid to 14.7 minutes for cystine stones. At a frequency of 170 kHz, the largest fragments for artificial stones were <4 mm. Exposures at 285 kHz produced only fragments <2 mm, and 800 kHz produced only fragments <1 mm.

Conclusions: Stone comminution with burst wave lithotripsy is feasible and is a potential noninvasive treatment method for nephrolithiasis. Adjusting the fundamental ultrasound frequency allows control of stone fragment size.

Introduction

Surgical management of urolithiasis has changed significantly since shock wave lithotripsy (SWL) in the early 1980's[1,2,3,4]. This technology, along with the development of endoscopic techniques such as ureteroscopy[5] and percutaneous nephrolithotomy[6,7] have almost completely replaced open surgery as a treatment option[8,9]. While minimally invasive methods continue to be refined, SWL may be an extracorporeal procedure for stone disintegration. We are exploring a new approach to extracorporeal lithotripsy that applies broadly focused, sinusoidal ultrasound bursts rather than shock waves to fragment stones. Burst wave lithotripsy (BWL) uses a focused source to generate pressure pulses that can be transcutaneously administered. The bursts are delivered in a broadly focused beam to efficiently generate stresses within the stone. In addition, relatively low pressure amplitudes are applied to prevent accumulation of cavitation bubbles that can shield acoustic waves from propagating into the stone[17]. The purpose of this study was to examine the feasibility of stone fracture by BWL applied to both artificial and natural calculi in vitro.

Materials and Methods

Artificial and Natural Stone Preparation

Artificial stones were created using a model developed by Liu and Zhong[18], which have acoustic properties similar to natural calcium oxalate monohydrate (COM) stones. Begostone plaster powder was mixed with deionized, degassed water in a ratio of 5:1 by weight. Aliquots of the mixture were then pipetted into an acetal plastic mold to form cylindrical stones of 6 mm diameter and 10-12 mm length. The mold was placed in a water bath 30 minutes after pipetting and allowed to further set for at least 12 hours. The stones were then removed from the mold and placed in deionized water until use in the experiments.

Human stones with primary compositions of uric acid, magnesium ammonium phosphate (struvite), COM, and cystine were also obtained for experiments. The largest dimension of each stone was between 5-15 mm (mean 8.2+/−3.0 mm). The stones were submerged in deionized water at least 72 hours prior to treatment.

Burst Wave Lithotripsy System

Exposures were performed using three piezoelectric focused ultrasound transducers with operating frequencies of 170 kHz, 285 kHz, and 800 kHz. The transducers were driven by a high-voltage radiofrequency amplifier19 controlled with a field-programmable gate array board (DEI, Altera, San Jose, Calif., USA). Each transducer was calibrated using a fiber optic hydrophone (FOPH2000, RP Acoustics, Leutenbach, Germany) to measure the pressure waveforms in the focal region and effective beamwidth in a degassed water bath. The focus of each ultrasound transducer was defined by an ellipsoidal region of high pressure amplitude. The 170 kHz transducer had an 80 mm aperture and a focal length of 54 mm. The −6 dB focal pressure beamwidth was 32.4 mm along the acoustic axis and 7.6 mm transverse. The 285 kHz transducer had a beamwidth of 42.0 mm axial and 5.6 mm transverse. The 800 kHz transducer had a beamwidth of 17.0 mm axial and 2.6 mm transverse. In order to permit an even comparison of the effect of the ultrasound frequency on stone comminution, the stones were aligned in a prefocal position when using the 285 kHz and 800 kHz transducers to match the beamwidth of the 170 kHz transducer and the pressure output of each transducer was adjusted such that the peak pressure amplitude in the plane aligned with the stone center was virtually the same for all three devices.

Stone Exposures

The transducer was positioned in a degassed and filtered water bath. A small amount of cyanoacrylate adhesive was used to affix the stone to a 25-μm thick acoustically-transparent polyester membrane attached over a polyvinyl chloride plastic hoop. This apparatus held the stone in a stable position during treatment to observe the progression of fragmentation and minimize reflections from the holder. The stone and holder were attached to a motorized, 3-axis positioning system (Velmex, Inc, Bloomfield, N.Y., USA) that allowed precise alignment of the stone with the focus. A digital camera was used to record images of stones and fragments before, during, and after acoustic exposure. Stones were exposed to ultrasound bursts with duration of 10 cycles and focal pressure amplitude $p_f \leq 6.5$ MPa. The number of bursts administered per second (burst repetition rate) was at 200 Hz. Note that the burst repetition rate is a separate parameter from the ultrasound frequency (which determines the rate of oscillations within a single burst). After treatment, stone fragments that dropped into a basket were collected and allowed to dry, then photographed and passed through a series of sieves to determine the fragment size distribution.

Figure 13:
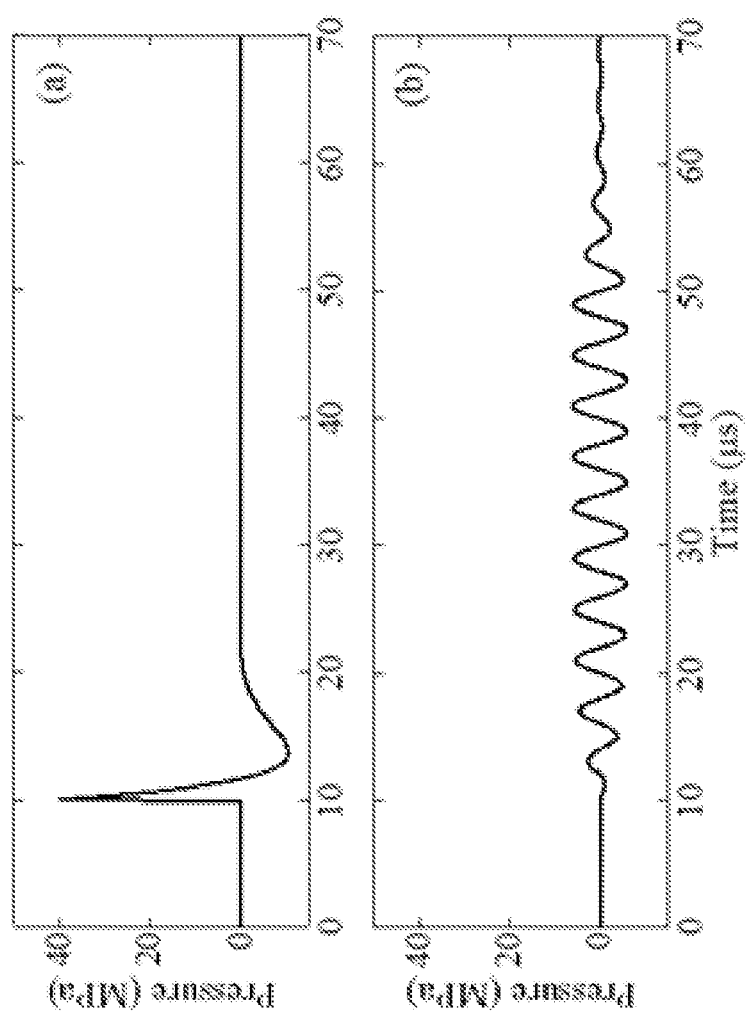
FIG. 13 shows aspects of a modeled focal pressure waveform for a lithotripsy shock wave (a) and BWL waveform (b) in accordance with one or more example embodiments.

FIG. 13 shows aspects of a modeled focal pressure waveform for a lithotripsy shock wave (a) and BWL waveform (b) in accordance with one or more example embodiments. The waveform in (a) approximates the shock from a Dornier HM3 lithotripter, while the burst wave in (b) corresponds with a pressure amplitude ($p_a=6.5$ MPa) applied here. The experimental setup for exposure of stones to burst waves is shown in (c). A focused ultrasound transducer was placed in water tank, and the stone was aligned with the focus using a motorized 3-axis positioning system. The transducer was driven by an amplifier to expose the stone to ultrasound bursts. Fragments were collected in a small container positioned below the stone.

Figure 14:
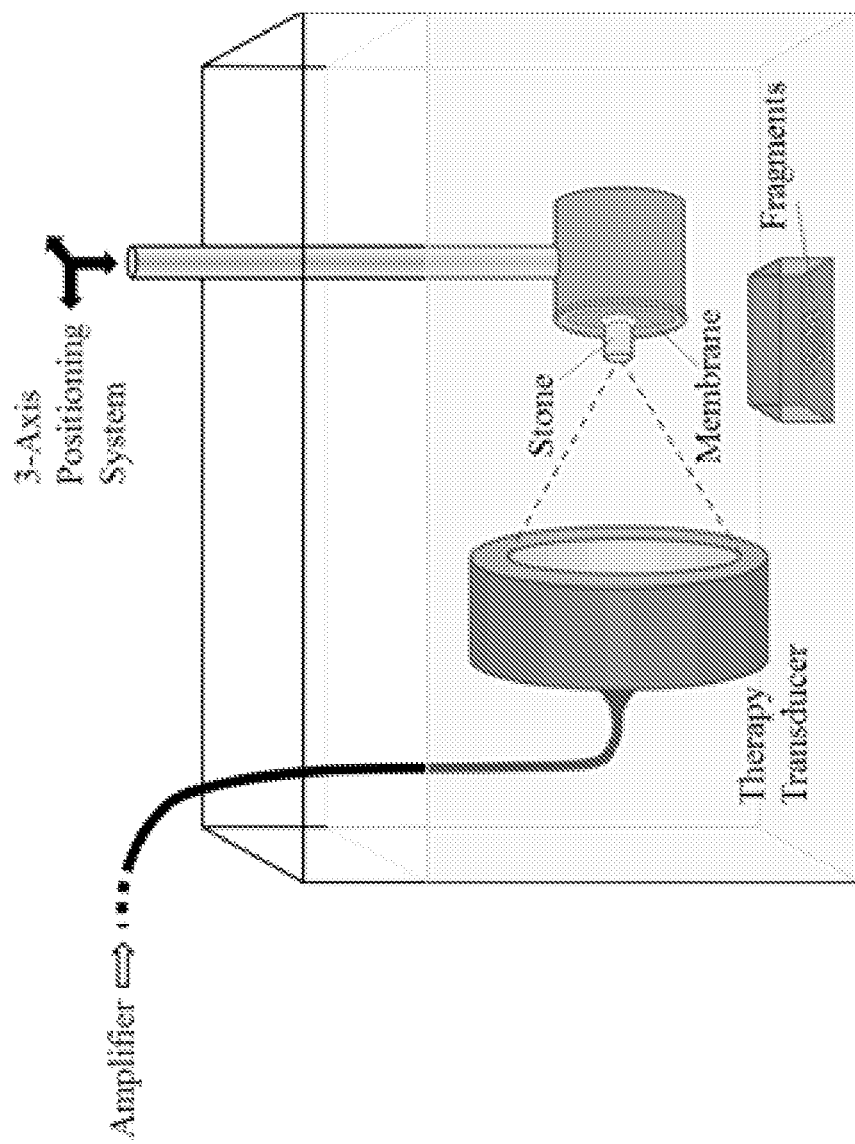
FIG. 14 shows aspects of an experimental setup for exposure of stones to BWL waveforms in accordance with one or more example embodiments.

FIG. 14 shows aspects of an experimental setup for exposure of stones to BWL waveforms in accordance with one or more example embodiments. The stone was affixed to a holder and placed in a tank of degassed water. A focused ultrasound transducer was placed in water tank and the stone was aligned with the focus using a motorized positioning system. The transducer was driven by an amplifier to expose the stone to ultrasound bursts. Fragments were collected in a small container positioned below the stone.

Several experiments were performed to evaluate the in vitro characteristics of stone fragmentation by BWL. First, to determine the pressure threshold for stone fragmentation artificial stones were treated for 5 minutes each at different pressure amplitudes (n=3 per amplitude, $P_f$=1.2 to 6.5 MPa) at 170 kHz. Second, to determine the effect of stone composition on stone fragmentation, both artificial (n=12) and natural stones (n=3 per composition) were exposed to the highest pressure amplitude ($P_f$=6.5 MPa) and the fragmentation process and size distribution were compared. Finally, to evaluate the effect of the ultrasound frequency on fragment size, artificial stones were exposed to ultrasound frequencies of 170 kHz, 285 kHz, and 800 kHz.

Results

Figure 15:
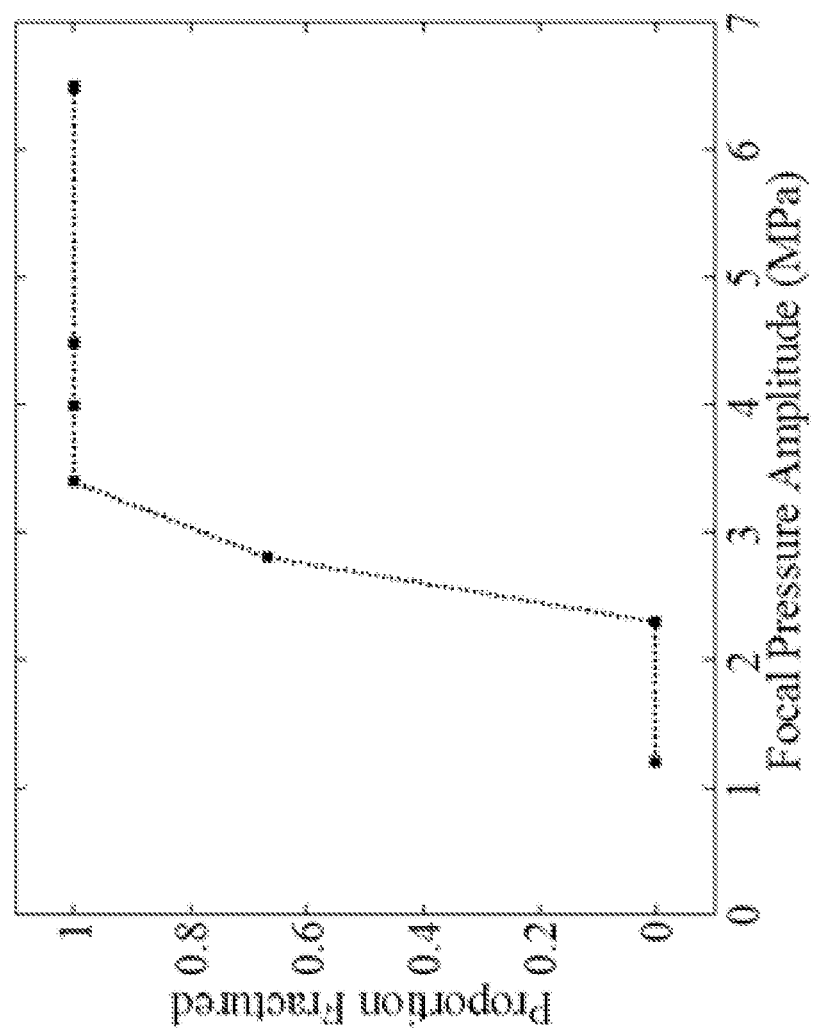
FIG. 15 shows aspects of a proportion of artificial stones containing fractures in accordance with one or more example embodiments.

Erosion and multiple fractures were observed in stones treated at 170 kHz when the focal pressure amplitudes were $P_f \geq 2.8$ MPa (FIG. 15). At the next lowest pressure amplitude ($P_f$=2.3 MPa) and below, no change in the stones was visible over the exposure duration of 5 minutes (60,000 bursts). Above $P_f$=2.3 MPa, very fine dust was emitted from the stone, and fracture lines were observed on the stone surface, predominantly aligned along the circumferential and longitudinal directions of the cylindrical stone. Subsequently, fragments separated from the stone, with the fragment geometry resulting from the position of these fractures. Fragmentation generally initiated at the surface of the stone nearest the therapy transducer and proceeded distally until the entire stone was disintegrated into fragments, with the exception of a small portion directly adhered to the membrane (FIG. 3). The artificial stones treated at pressure amplitude $P_f$=6.5 MPa (n=12) required 9.7±2.8 minutes (mean±SD) to achieve complete fragmentation.

FIG. 15 shows aspects of a proportion of artificial stones containing fractures in accordance with one or more example embodiments. The fractures were created after exposure of 60,000 bursts as a function of focal pressure amplitude. At each pressure level, n=3 stones were tested.

Figure 16:
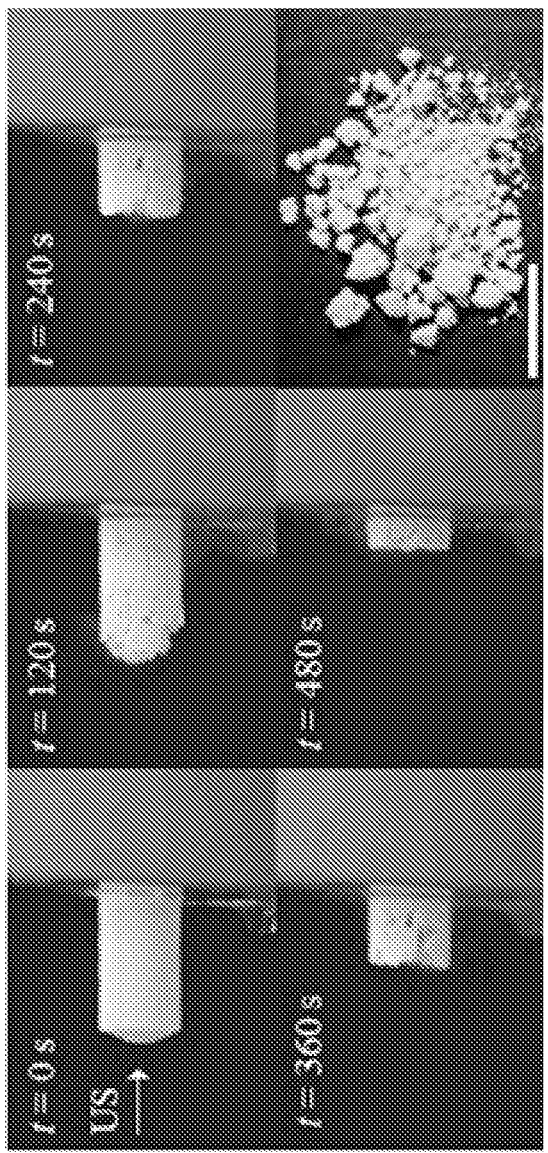
FIG. 16 shows aspects of a photographic sequence of an artificial stone in accordance with one or more example embodiments.

FIG. 16 shows aspects of a photographic sequence of an artificial stone in accordance with one or more example embodiments. The sequence illustrates the artificial stone during exposure to 170 kHz bursts with $P_f$=6.5 MPa over 8 minutes. Ultrasound burst waves are incident on the stone from the left. The photograph to the right shows the fragments generated after 8 minutes of exposure. The scale bar is 1 cm.

In the second series of experiments, natural stones of four different compositions exposed to 170 kHz bursts at the pressure amplitude ($P_f$=6.5 MPa) were successfully reduced to fragments (FIG. 4). The progression of treatment and resulting fragmentation proceeded similarly to that observed with the artificial stones. However, the time required to achieve fragmentation varied greatly with stone type. For instance, a 7-mm struvite stone could be fragmented in 4 seconds (800 bursts), while a similarly sized cystine stone required 10.3 minutes (123,600 bursts). The range of treatment times was 0.17-1.40 minutes for uric acid, 0.07-2.02 minutes for struvite, 8.0-18.1 minutes for COM, and 10.3-21.3 minutes for cystine stones.

Figure 17:
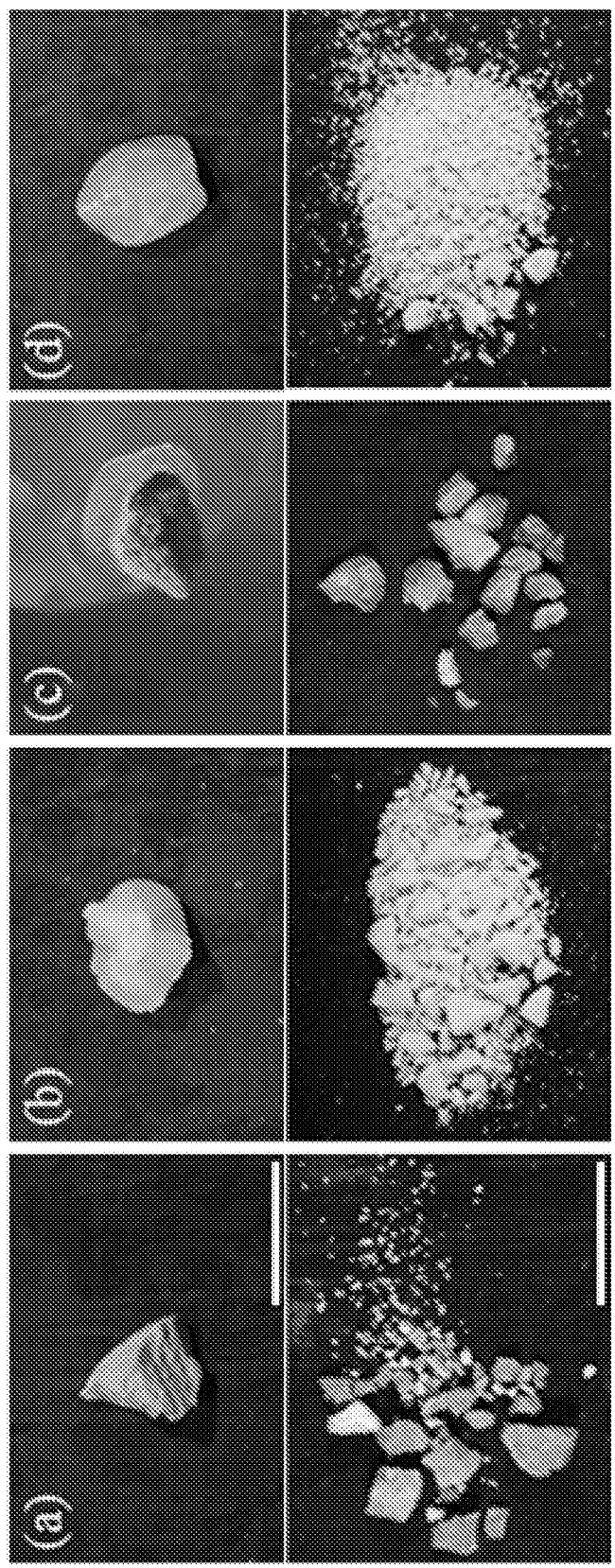
FIG. 17 shows aspects of uric acid (a), struvite (b), COM (c), and cystine (d) stones in accordance with one or more example embodiments.

FIG. 17 shows aspects of uric acid (a), struvite (b), COM (c), and cystine (d) stone in accordance with one or more example embodiments. The top images show the stone before 170-kHz burst wave exposure, and the bottom shows after treatment. The scale bars in (d) are 1 cm. All images have identical scales.

The sizes of fragments produced by each treatment were consistent among stones of the same composition. FIG. 5 shows the distribution of the collected fragments as a proportion of the total mass of the stone, as obtained by sequential sieving. While variations in the distribution of fragment sizes can be seen between different stone types, the largest fragments produced for each type were similar in size. None of the treatments produced fragments >4 mm. The largest fragments were 3-4 mm for COM, uric acid, and artificial stones, and 2-3 mm for struvite and cystine stones. A majority of the fragment mass was <3 mm for COM and uric acid, <2 mm for artificial, and <1 mm for struvite and cystine stones.

In the third series of experiments, artificial stones treated with exposures at three frequencies were compared. At 170 kHz, circumferential fractures in the stone appeared evenly spaced, approximately 3 mm apart and did not appear to change with pressure amplitude. Exposures at 285 kHz and 800 kHz produced more closely spaced fractures in the stone, and resulted in smaller fragments compared with treatments at 170 kHz (FIGS. 5 and 6). At 285 kHz, no fragments larger than 2 mm were generated, and at 800 kHz, no fragments larger than 1 mm were generated.

Figure 18:
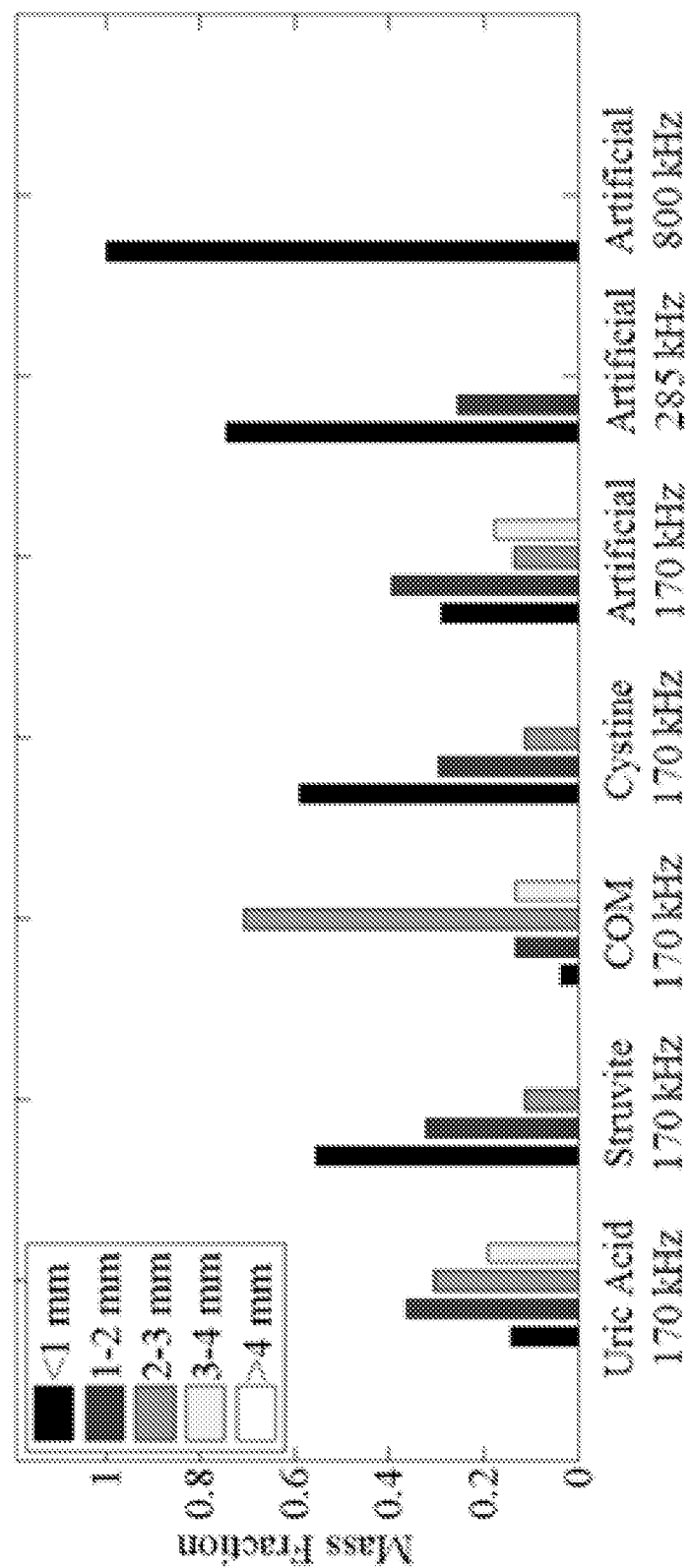
FIG. 18 shows aspects of a distribution of fragments in accordance with one or more example embodiments.

FIG. 18 shows aspects of a distribution of fragments in accordance with one or more example embodiments. The size distribution of fragments were post-exposure measured by serial sieving of fragments. The left 4 groups show the size distribution of fragments for natural stones treated with 170 kHz bursts, while the right 3 groups show the size distribution of artificial stones treated with 170 kHz, 285 kHz, and 800 kHz bursts. All measurements are mean values for stones treated in each category. COM=calcium oxalate monohydrate.

Figure 19:
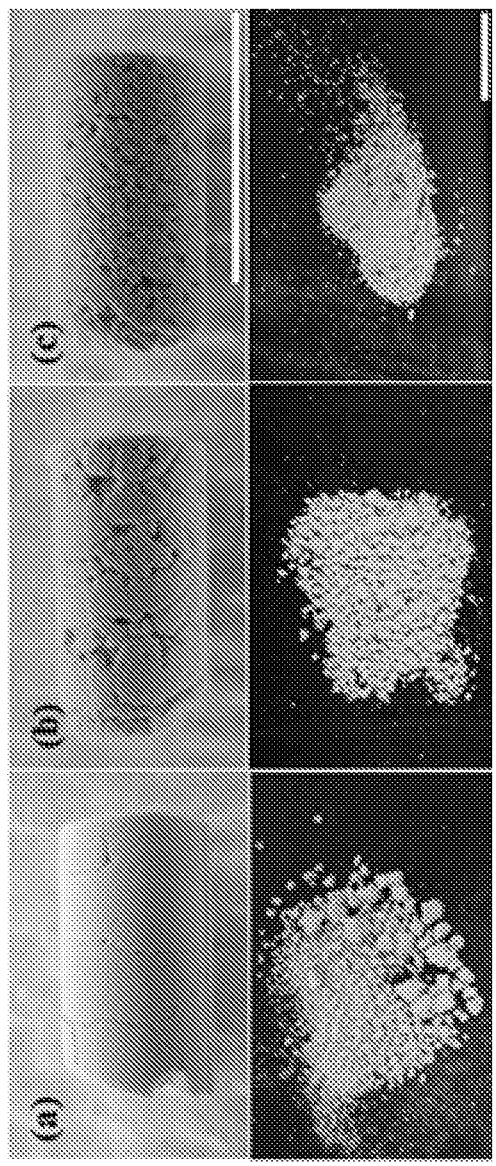
FIG. 19 shows aspects of fractures and fragments in accordance with one or more example embodiments.

FIG. 19 shows aspects of fractures and fragments in accordance with one or more example embodiments. The fractures (top) and fragments (bottom) generated for stones treated with 170 kHz (a), 285 kHz (b), and 800 kHz (c) bursts with similar peak pressure amplitude applied to the stone. As the treatment frequency increased, the stone surface fractures become closer together and the fragments produced decreased in size. Bursts were incident from the left in each of the photographs of stone fractures. The scale bars for the top and bottom rows are both 1 cm.

Discussion

SWL has been the sole extracorporeal therapy for renal stones for more than 30 years. While the physical mechanisms of shock wave-induced stone fracture were not fully understood during its clinical introduction, subsequent research has identified two particularly important effects[15,20].

First, a focus broader than the stone creates shear waves that cause internal tension, leading to growth of fractures and fragmentation[15,21]. Second, shock-induced cavitation at the stone surface can initiate these fractures[13,16]. At the same time, proliferation of cavitation clouds caused by delivering shocks at too great of a rate tends to reduce their effectiveness[17] and can lead to tissue damage[22]. In the present study, we employed bursts that were broadly focused to generate shear, and sought to avoid cavitation clouds by using relatively low-pressure pulses that could be delivered at a fast repetition rate to maximize the energy transferred into the stone. Provided such bursts produce the necessary tension within the stone to generate and propagate fractures, a shocked waveform is not required to produce comminution.

Another technique using focused ultrasound has also been reported, but takes an alternative approach relying solely on cavitation[23,24]. Under this modality, ultrasound is strongly focused onto the stone surface to generate a localized cloud of cavitation. While the cloud likely minimizes acoustic propagation within the stone, cavitation collapses against its surface can reduce it to very fine dust through surface erosion. While this technique has not yet been demonstrated in vivo, it may also provide better control of fragment size compared to SWL. The results demonstrate that broadly focused burst waves are capable of fracturing stones of varying composition, including some considered to be resistant to SWL such as cystine[25,26]. While we did not measure the threshold to fragment natural calculi, artificial stones could be treated at focal pressures as low as 2.8 MPa. This level is at least an order of magnitude lower than shock amplitudes for SWL in practice (30100 MPa), although it has also been demonstrated by Eisenmenger that fracture of artificial stones can be accomplished with shock amplitudes as low as 11 MPa[27]. Though lower pressure amplitudes were applied, bursts were administered at a much greater rate (200 Hz here) than a typical SWL pulse repetition rate (1-2 Hz). The result of this rapid delivery of energy to the stone is evident particularly with the softer stone compositions (uric acid and struvite), which underwent fragmentation in only a few seconds in some experiments. COM and cystine stones required longer exposures, but all treatments achieved complete comminution of the stones into clinically passable fragments (≤4 mm). While current practice applies a fairly consistent dose of shock waves (2000-3000 per session), these results suggest that different stone types may require greatly different amounts of energy to fracture, and feedback on treatment progression could be valuable in efficiently achieving a therapeutic endpoint.

One advantage of this form of therapy over SWL may be the ability to control the size of the fragments, which is clinically relevant to produce stone fragments that are passable through the urinary tract. Treatments with a 170 kHz transducer produced fragments of similar size for different stone types, with maximum fragment sizes of ~3 mm. Studies exposing stones at 3 different frequencies suggested that higher frequencies generate more densely-spaced fractures, resulting in smaller fragments. Our simulations and experiments indicate that bursts between 400-500 kHz would generate fragments ~1 mm maximum, which might be clinically ideal.

The in vitro experimental setup used here performed exposures on fixed stones in a specific orientation. While this allowed us to examine the repeatable characteristics of stone fracture, a free stone would more accurately simulate a physiologic situation. The fragments did not remain in the focus for the duration of treatment, but rather fell out after separation from the stone. It could be argued that these fragments would likely be further reduced in size had they been allowed to remain in or near the focus for the treatment duration. An additional limitation of this preliminary study was that several of the burst parameters were necessarily fixed. Future work should explore the effects of changing parameters such as burst length, burst repetition frequency, and amplitude, guided by theoretical and experimental analysis of the physical mechanisms.

Conclusions

This study demonstrated the feasibility of fragmenting urinary calculi using broadly focused ultrasound bursts. Bursts were observed to produce fractures in artificial and human calculi that led to fragmentation of all stone types. The duration of exposure required to reduce stones to passable fragments varied with stone type. The size of the resultant stone fragments could be controlled by adjusting ultrasound frequency. These characteristics indicate BWL may offer a potentially viable noninvasive alternative to SWL.

References

[1] G. Bandi, S. L. Best and S. Y. Nakada, "Current practice patterns in the management of upper urinary tract calculi in the north central United States." J Endourol 22, 631-636 (2008).

[2] V. G. Bird, B. Fallon and H. N. Winfield, "Practice patterns in the treatment of large renal stones." J Endourol 17, 355-363 (2003).

[3] B. R. Matlaga, "Contemporary surgical management of upper unnary tract calculi." J Urol 181, 2152-2156 (2009).

[4] C. Chaussy, E. Schmiedt, D. Jocham, W. Brendel, B. Forssmann and V. Walther, "First clinical experience with extracorporeally induced destruction of kidney stones by shock waves." J Urol 127, 417-420 (1982).

[5] S. R. Payne, T. F. Ford and J. E. Wickham, "Endoscopic management of upper urinary tract stones." Br J Surg 72, 822-824 (1985).

[6] R. V. Clayman, V. Surya, R. P. Miller, W. R. Castaneda-Zuniga, A. D. Smith, D. H. Hunter, K. Amplatz and P. H. Lange, "Percutaneous nephrolithotomy: Extraction of renal and ureteral calculi from 100 patients." J Urol 131, 868-871 (1984).

[7] J. E. Wickham and M. J. Kellett, "Percutaneous nephrolithotomy." Br J Urol 53, 297-299 (1981).

[8] M. L. Paik, M. A. Wainstein, J. P. Spirnak, N. Hampel and M. I. Resnick, "Current indications for open stone surgery in the treatment of renal and ureteral calculi." J Urol 159, 374-378; discussion 378-379 (1998).

[9]B. R. Matlaga and D. G. Assimos, "Changing indications of open stone surgery." Urology 59, 490-493; discussion 493-494 (2002).

[10]R. Gerber, U. E. Studer and H. Danuser, "Is newer always better? A comparative study of 3 lithotriptor generations." J Urol 173, 2013-2016 (2005).

[11]J. M. Teichman, A. J. Portis, P. P. Cecconi, W. L. Bub, R. C. Endicott, B. Denes, M. S. Pearle and R. V. Clayman, "In vitro comparison of shock wave lithotripsy machines." J Urol 164, 1259-1264 (2000).

[12]W. Eisenmenger, X. X. Du, C. Tang, S. Zhao, Y. Wang, F. Rong, D. Dai, M. Guan and A. Qi, "The first clinical results of "wide-focus and low-pressure" ESWL." Ultrasound Med Biol 28, 769-774 (2002).

[13]D. Howard and B. Sturtevant, "In vitro study of the mechanical effects of shock-wave lithotripsy." Ultrasound Med Biol 23, 1107-1122 (1997).

[14]S. Zhu, F. H. Cocks, G. M. Preminger and P. Zhong, "The role of stress waves and cavitation in stone comminution in shock wave lithotripsy." Ultrasound Med Biol 28, 661-671 (2002).

[15]O. A. Sapozhnikov, A. D. Maxwell, B. MacConaghy and M. R. Bailey, "A mechanistic analysis of stone fracture in lithotripsy." J Acoust Soc Am 121, 1190-1202 (2007).

[16]K. Kerbl, J. Rehman, J. Landman, D. Lee, C. Sundaram and R. V. Clayman, "Current management of urolithiasis: Progress or regress?" J Endourol 16, 281-288 (2002). [17]Y. A. Pishchalnikov, J. A. McAteer, J. C. Williams, Jr., I. V. Pishchalnikova and R. J. Vonderhaar, "Why stones break better at slow shockwave rates than at fast rates: In vitro study with a research electrohydraulic lithotripter." J Endourol 20, 537-541 (2006).

[18]Y. Liu and P. Zhong, "Begostone—a new stone phantom for shock wave lithotripsy research." J Acoust Soc Am 112, 1265-1268 (2002).

[19]T. L. Hall and C. A. Cain A low cost, compact, 512 channel therapeutic system for transcutaneous ultrasound surgery. International symposium on therapeutic ultrasound, AIP Conf Proc, 445-449 (2005).

[20]S. Zhu, F. H. Cocks, G. M. Preminger and P. Zhong, "The role of stress waves and cavitation in stone comminution in shock wave lithotripsy." Ultrasound Med Biol 28, 661-671 (2002).

[21]R. O. Cleveland and O. A. Sapozhnikov, "Modeling elastic wave propagation in kidney stones with application to shock wave lithotripsy." J Acoust Soc Am 118, 2667-2676 (2005).

[22]P. M. Blomgren, B. A. Connors, J. E. Lingeman, L. R. Willis and A. P. Evan, "Quantitation of shock wave lithotripsy-induced lesion in small and large pig kidneys." Anat Rec 249, 341-348 (1997).

[23]T. Ikeda, S. Yoshizawa, M. Tosaki, J. S. Allen, S. Takagi, N. Ohta, T. Kitamura and Y. Matsumoto, "Cloud cavitation control for lithotripsy using high intensity focused ultrasound." Ultrasound Med Biol 32, 1383-1397 (2006).

[24]A. P. Duryea, T. L. Hall, A. D. Maxwell, Z. Xu, C. A. Cain and W. W. Roberts, "Histotripsy erosion of model urinary calculi." J Endourol 25, 341-344 (2011).

[25]S. B. Streem, "Contemporary clinical practice of shock wave lithotripsy: A reevaluation of contraindications." J Urol 157, 1197-1203 (1997).

[26]J. C. Williams, Jr., K. C. Saw, R. F. Paterson, E. K. Hatt, J. A. McAteer and J. E. Lingeman, "Variability of renal stone fragility in shock wave lithotripsy." Urology 61, 1092-1096; discussion 1097 (2003).

[27]W. Eisenmenger, "The mechanisms of stone fragmentation in eswl." Ultrasound Med Biol 27, 683-693 (2001).

[28]B. R. Matlaga, J. A. McAteer, B. A. Connors, R. K. Randa, A. P. Evan, J. C. Williams, J. E. Lingeman and L. R. Willis, "Potential for cavitation-mediated tissue damage in shockwave lithotripsy." J Endourol 22, 121-126 (2008).

[29]B. A. Connors, J. A. McAteer, A. P. Evan, P. M. Blomgren, R. K. Randa, C. D. Johnson, S. Gao, Y. A. Pishchalnikov and J. E. Lingeman, "Evaluation of shock wave lithotripsy injury in the pig using a narrow focal zone lithotriptor." BJU Int 110, 1376-1385 (2012).

[30]A. P. Evan, J. A. McAteer, B. A. Connors, Y. A. Pishchalnikov, R. K. Randa, P. Blomgren, L. R. Willis, J. C. Williams, Jr., J. E. Lingeman and S. Gao, "Independent assessment of a wide-focus, low-pressure electromagnetic lithotripter: Absence of renal bioeffects in the pig." BJU Int 101, 382-388 (2008).

5. Conclusion

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying Figures. In the Figures, similar symbols typically identify similar components, unless context dictates otherwise. It will be readily understood that the aspects of the present disclosure, as generally described herein, and illustrated in the Figures, can be arranged, substituted, combined, separated, and designed in a wide variety of different configurations, all of which are explicitly contemplated herein.

With respect to any or all of the diagrams, scenarios, and flow charts in the Figures and as discussed herein, each block and/or communication can represent a processing of information and/or a transmission of information in accordance with example embodiments. Alternative embodiments are included within the scope of these example embodiments. In these alternative embodiments, for example, functions described as blocks, transmissions, communications, requests, responses, and/or messages can be executed out of order from that shown or discussed, including substantially concurrent or in reverse order, depending on the functionality involved. Further, more or fewer blocks and/or functions can be used with any of the ladder diagrams, scenarios, and flow charts discussed herein, and these ladder diagrams, scenarios, and flow charts can be combined with one another, in part or in whole.

A block that represents a processing of information can correspond to circuitry that can be configured to perform the specific logical functions of a herein-described method or technique. Alternatively or additionally, a block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk or hard drive or other storage medium.

The computer readable medium can also include physical and/or non-transitory computer readable media such as computer-readable media that stores data for short periods of time like register memory, processor cache, and random access memory (RAM). The computer readable media can also include physical and/or non-transitory computer readable media that stores program code and/or data for longer periods of time, such as secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

Moreover, a block that represents one or more information transmissions can correspond to information transmissions between software and/or hardware modules in the same physical device. However, other information transmissions can be between software modules and/or hardware modules in different physical devices.

The particular arrangements shown in the Figures should not be viewed as limiting. It should be understood that other embodiments can include more or less of each element shown in a given Figure. Further, some of the illustrated elements can be combined or omitted. Yet further, an example embodiment can include elements that are not illustrated in the Figures.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for attempting to fragment or comminute an object in a body using ultrasound, the method comprising:
   a step of producing a burst wave lithotripsy (BWL) waveform by a therapy transducer, wherein the BWL waveform is configured to fragment or comminute the object without conducting a shockwave lithotripsy procedure prior to the step of producing the BWL waveform, wherein the BWL waveform comprises a first burst of continuous ultrasound cycles and a second burst of continuous ultrasound cycles, wherein the continuous ultrasound cycles of the first and second burst are sinusoidal, and wherein a burst frequency corresponds to a frequency of repeating the bursts of the BWL waveform;
   during a first burst time, transmitting a first plurality of the continuous ultrasound cycles in the first burst of the BWL waveform toward the object at a cycle frequency f, a positive peak pressure amplitude less than 10 MPa, and a negative peak pressure amplitude greater than −9 MPa;
   during a rest time, not transmitting the continuous ultrasound cycles, wherein the rest time separates the first burst from the second burst;
   during a second burst time, transmitting a second plurality of the continuous ultrasound cycles in the second burst of the BWL waveform toward the object at the cycle frequency f, the positive peak pressure amplitude less than 10 MPa, and the negative peak pressure amplitude greater than −9 MPa; and
   repeating, at the burst frequency, transmissions of the bursts of the continuous ultrasound cycles separated by the rest time.

2. The method of claim 1, wherein the burst frequency is in a range from 3 Hz to 11 kHz, and wherein the cycle frequency f is in a range from 100 kHz to 1 MHz.

3. The method of claim 1, wherein the cycle frequency f of the first burst and the second burst is a first cycle frequency, the method further comprising:
   during a third burst time, transmitting a third plurality of sinusoidal ultrasound cycles in the third burst of the BWL waveform toward the object at a second cycle frequency,
   wherein the second cycle frequency is different from the first cycle frequency.

4. The method of claim 1, wherein the first burst time is in a range from 1 microsecond to 1 millisecond.

5. The method of claim 1, wherein the object is at least one of the following: a urinary tract stone, a kidney stone, a ureter stone, a bladder stone, a urethra stone, a prostate stone, a salivary stone, a gallbladder stone, a gall stone, a bile duct, a blood clot, blood, mucous, stool, cerumen, bodily tissue, a calcification, a calcified plaque, an atherosclerotic plaque, uric acid, struvite, calcium oxalate monohydrate (COM), cystine, a tonsil stone, an artificial object, and an object introduced inside the subject.

6. The method of claim 1, further comprising:
   producing, by an imaging transducer, one or more imaging signals that reflect from the object and return to the imaging transducer, and
   causing a graphical display to provide a visual indication of the object in the body.

7. The method of claim 6, wherein the object comprises one or more surfaces, and wherein a beam width of the BWL waveform is broader than the object.

8. The method of claim 1, wherein the continuous ultrasound cycles within the bursts of the BWL waveform have the positive peak pressure amplitude in a range from greater than 2.8 MPa to less than 10 MPa.

9. The method of claim 1, wherein the continuous ultrasound cycles within the bursts of the BWL waveform have the negative peak pressure amplitude in a range from less than −7 MPa to greater than −9 MPa.

10. The method of claim 1, wherein the continuous ultrasound cycles within the bursts of the BWL waveform have the negative peak pressure amplitude greater than −8 MPa.

11. The method of claim 1, wherein the continuous ultrasound cycles within the bursts of the BWL waveform have the negative peak pressure amplitude greater than −7 MPa.

12. The method of claim 1, wherein the continuous ultrasound cycles within the bursts of the BWL waveform have the positive peak pressure amplitude less than 8 MPa.

13. An ultrasound device for attempting to fragment or comminute an object in a body by ultrasound, comprising:
   a processor;
   a therapy transducer; and
   a non-transitory computer-readable medium configured to store program instructions that, when executed by the processor, cause the ultrasound device to carry out functions comprising:
      a step of producing a burst wave lithotripsy (BWL) waveform by the therapy transducer, wherein the BWL waveform is configured to fragment or comminute the object without conducting a shockwave lithotripsy procedure prior to the step of producing the BWL waveform, wherein the BWL waveform comprises a first burst of continuous ultrasound cycles and a second burst of continuous ultrasound cycles, wherein the continuous ultrasound cycles of the first and second burst are sinusoidal, and wherein a burst frequency corresponds to a frequency of repeating the bursts of the BWL waveform;

during a first burst time, transmitting a first plurality of the continuous ultrasound cycles in the first burst of the BWL waveform toward the object at a cycle frequency f, a positive peak pressure amplitude less than 10 MPa, and a negative peak pressure amplitude greater than −9 MPa;

during a rest time, not transmitting the continuous ultrasound cycles, wherein the rest time separates the first burst from the second burst;

during a second burst time, transmitting a second plurality of the continuous ultrasound cycles in the second burst of the BWL waveform toward the object at the cycle frequency f, the positive peak pressure amplitude less than 10 MPa, and the negative peak pressure amplitude greater than −9 MPa; and repeating, at the burst frequency, transmissions of the bursts of the continuous ultrasound cycles separated by the rest time.

14. The device of claim 13, wherein the burst frequency is in a range from 3 Hz to 11 kHz, and wherein the cycle frequency is in a range from 100 kHz to 1 MHz.

15. The device of claim 13, wherein the cycle frequency f of the first burst and the second burst is a first cycle frequency, the functions carried out by the ultrasound device further comprising:

during a third burst time, transmitting a third plurality of sinusoidal ultrasound cycles in a third burst of the BWL waveform toward the object at a second cycle frequency, wherein the second cycle frequency is different from the first cycle frequency.

16. The device of claim 13, wherein the functions carried out by the ultrasound device further comprise:

producing one or more imaging signals that reflect from the object and return to the computing device, and causing a graphical display of the computing device to provide a visual indication of the object in the body.

17. The device of claim 13, wherein the continuous ultrasound cycles within the bursts of the BWL waveform have the positive peak pressure amplitude in a range from greater than 2.8 MPa to less than 10 MPa.

18. The device of claim 13, wherein the continuous ultrasound cycles within the bursts of the BWL waveform have the negative peak pressure amplitude in a range from less than −7 MPa to greater than −9 MPa.

19. The device of claim 13, wherein the object is at least one of the following: a urinary tract stone, a kidney stone, a ureter stone, a bladder stone, a urethra stone, a prostate stone, a salivary stone, a gallbladder stone, a gall stone, a bile duct, a blood clot, blood, mucous, stool, cerumen, bodily tissue, a calcification, a calcified plaque, an atherosclerotic plaque, uric acid, struvite, calcium oxalate monohydrate (COM), cystine, a tonsil stone, an artificial object, and an object introduced inside the subject.

20. A method for attempting to fragment or comminute an object in a body using ultrasound, the method comprising:

a step of producing a burst wave lithotripsy (BWL) waveform by a therapy transducer, wherein the BWL waveform is configured to fragment or comminute the object without conducting a shockwave lithotripsy procedure prior to the step of producing the BWL waveform, wherein the BWL waveform comprises a first burst of continuous ultrasound cycles and a second burst of continuous ultrasound cycles, wherein the continuous ultrasound cycles of the first and second burst are sinusoidal, and wherein a burst frequency corresponds to a frequency of repeating the bursts of the BWL waveform; during a first burst time, transmitting a first plurality of the continuous ultrasound cycles in the first burst of the BWL waveform toward the object at a cycle frequency f, a positive peak pressure amplitude less than 10 MPa, and a negative peak pressure amplitude greater than −9 MPa;

during a rest time, not transmitting the continuous ultrasound cycles, wherein the rest time separates the first burst from the second burst; during a second burst time, transmitting a second plurality of the continuous ultrasound cycles in the second burst of the BWL waveform toward the object at the cycle frequency f, the positive peak pressure amplitude less than 10 MPa, and the negative peak pressure amplitude greater than −9 MPa; and repeating, at the burst frequency, transmissions of the bursts of the BWL waveform, wherein the bursts of the BWL waveform separated by the rest times are repeatedly transmitted from 20 times to 39,600,000 times.

21. The method of claim 20, wherein the bursts of the BWL waveform separated by the rest times are repeatedly transmitted from 20 times to 13,860,000 times.

22. The method of claim 20, wherein the bursts of the BWL waveform separated by the rest times are repeatedly transmitted from 20 times to 123,600 times.

23. The method of claim 20, wherein the cycle frequency f is in a range from 100 kHz to 1 MHz.

24. The method of claim 20, wherein the continuous ultrasound cycles within the bursts of the BWL waveform have the positive peak pressure amplitude in a range greater than 2.8 MPa to less than 10 MPa.

25. The method of claim 20, wherein the continuous ultrasound cycles within the bursts of the BWL waveform have the negative peak pressure amplitude in a range from less than −7 MPa to greater than −9 MPa.

26. The method of claim 20, wherein the object is at least one of the following: a urinary tract stone, a kidney stone, a ureter stone, a bladder stone, a urethra stone, a prostate stone, a salivary stone, a gallbladder stone, a gall stone, a bile duct, a blood clot, blood, mucous, stool, cerumen, bodily tissue, a calcification, a calcified plaque, an atherosclerotic plaque, uric acid, struvite, calcium oxalate monohydrate (COM), cystine, a tonsil stone, an artificial object, and an object introduced inside the subject.

27. An ultrasound device for attempting to fragment or comminute an object in a body by ultrasound, comprising:

a processor;

a therapy transducer; and a non-transitory computer-readable medium configured to store program instructions that, when executed by the processor, cause the ultrasound device to carry out functions comprising:

a step of producing a burst wave lithotripsy (BWL) waveform by the therapy transducer, wherein the BWL waveform is configured to fragment or comminute the object without conducting a shockwave lithotripsy procedure prior to the step of producing the BWL waveform, wherein the BWL waveform comprises a first burst of continuous ultrasound cycles and a second burst of continuous ultrasound cycles, wherein the continuous ultrasound cycles of the first and second burst are sinusoidal, and wherein a burst frequency corresponds to a frequency of repeating the bursts of the BWL waveform;

during a first burst time, transmitting a first plurality of the continuous ultrasound cycles in the first burst of the BWL waveform toward the object at a cycle frequency f, a positive peak pressure amplitude less than 10 MPa, and a negative peak pressure amplitude greater than −9 MPa;

during a rest time, not transmitting the continuous ultrasound cycles, wherein the rest time separates the first burst from the second burst;

during a second burst time, transmitting a second plurality of the continuous ultrasound cycles in the second burst of the BWL waveform toward the object at the cycle frequency f, the positive peak pressure amplitude less than 10 MPa, and the negative peak pressure amplitude greater than −9 MPa; and repeating, at the burst frequency, transmissions of the bursts of the BWL waveform, wherein the bursts of the BWL waveform separated by the rest times are repeatedly transmitted from 20 times to 39,600,000 times.

28. The device of claim 27, wherein the bursts of the BWL waveform separated by the rest times are repeatedly transmitted between 20 times and 123,600 times.

29. The device of claim 27, wherein the continuous ultrasound cycles within the bursts of the BWL waveform have the positive peak pressure amplitude in a range from greater than 2.8 MPa to less than 10 Mpa and the negative peak pressure amplitude in a range from less than −7 MPa to greater than −9 MPa.

30. The device of claim 27, wherein the object is at least one of the following: a urinary tract stone, a kidney stone, a ureter stone, a bladder stone, a urethra stone, a prostate stone, a salivary stone, a gallbladder stone, a gall stone, a bile duct, a blood clot, blood, mucous, stool, cerumen, bodily tissue, a calcification, a calcified plaque, an atherosclerotic plaque, uric acid, struvite, calcium oxalate monohydrate (COM), cystine, a tonsil stone, an artificial object, and an object introduced inside the subject.

31. A method for attempting to fragment or comminute an object in a body using ultrasound, the method comprising:

a step of producing a burst wave lithotripsy (BWL) waveform by a therapy transducer, wherein the BWL waveform is configured to fragment or comminute the object without conducting a shockwave lithotripsy procedure prior to the step of producing the BWL waveform, wherein the BWL waveform comprises a first burst of continuous ultrasound cycles and a second burst of continuous ultrasound cycles, wherein the continuous ultrasound cycles of the first and second burst are sinusoidal, and wherein a burst frequency corresponds to a frequency of repeating the bursts of the BWL waveform;

during a first burst time, transmitting a first plurality of the continuous ultrasound cycles in the first burst of the BWL waveform toward the object at a cycle frequency f, wherein a negative peak pressure amplitude is greater than −9 MPa;

during a rest time, not transmitting the continuous ultrasound cycles, wherein the rest time separates the first burst from the second burst;

during a second burst time, transmitting a second plurality of the continuous ultrasound cycles in the second burst of the BWL waveform toward the object at the cycle frequency f, wherein the negative peak pressure amplitude is greater than −9 MPa; and repeating, at the burst frequency, transmissions of the bursts of the continuous ultrasound cycles separated by the rest time.

* * * * *